US012295589B2

(12) United States Patent
Amiot et al.

(10) Patent No.: US 12,295,589 B2
(45) Date of Patent: May 13, 2025

(54) METHOD, SURGICAL APPARATUS, AND SURGICAL IMPLANT FOR MINIMALLY INVASIVE SURGICAL PROCEDURES

(71) Applicant: RELJA Innovations, LLC, Brookfield, WI (US)

(72) Inventors: Robby A. Amiot, Brookfield, WI (US); Joseph P. Ritz, Castroville, TX (US); Eric Marcano, San Antonio, TX (US)

(73) Assignee: RELJA Innovations, LLC, Brookfield, WI (US)

( * ) Notice: Subject to any disclaimer, the term of this patent is extended or adjusted under 35 U.S.C. 154(b) by 262 days.

(21) Appl. No.: 17/637,292

(22) PCT Filed: Dec. 9, 2020

(86) PCT No.: PCT/US2020/064002
§ 371 (c)(1),
(2) Date: Feb. 22, 2022

(87) PCT Pub. No.: WO2021/119122
PCT Pub. Date: Jun. 17, 2021

(65) Prior Publication Data
US 2023/0000498 A1 Jan. 5, 2023

Related U.S. Application Data

(60) Provisional application No. 62/947,376, filed on Dec. 12, 2019.

(51) Int. Cl.
*A61B 17/15* (2006.01)
*A61B 17/16* (2006.01)
(Continued)

(52) U.S. Cl.
CPC ........ *A61B 17/151* (2013.01); *A61B 17/1615* (2013.01); *A61B 17/1775* (2016.11);
(Continued)

(58) Field of Classification Search
CPC .............. A61B 17/151; A61B 17/1775; A61B 17/8897; A61B 17/02; A61B 17/15;
(Continued)

(56) References Cited

U.S. PATENT DOCUMENTS 5,030,219 A * 7/1991 Matsen, III ........ A61B 17/1778
606/86 R
6,391,031 B1 5/2002 Toomey
(Continued)

FOREIGN PATENT DOCUMENTS

DE 102008004922 A1 7/2009
WO 2020139938 A1 7/2020
(Continued)

OTHER PUBLICATIONS

International Search Report Apr. 28, 2021.

*Primary Examiner* — Marcela I. Shirsat
(74) *Attorney, Agent, or Firm* — Wong Meyer Smith & McConnell

(57) ABSTRACT

A minimally invasive precision cutting guide, targeting guide, implant, and other instruments comprise a system that permits a physician to surgically correct a bunion or similar deformity with a minimum disruption of surrounding soft tissue. The precision cutting guide ensures that the physician cuts bone in the proper location and orientation. Each of the instruments is designed to minimize disruption to surrounding soft tissue. The system also precisely locates an orthopedic implant such that it can fixate two bone fragments after an osteotomy, or two bones after surgery. The precision cutting guide, targeting guide, implant, and other instruments are provided in a sterile kit for the convenience of the surgeon and safety of the patient.

20 Claims, 27 Drawing Sheets

(51) Int. Cl.
  *A61B 17/17* (2006.01)
  *A61B 17/56* (2006.01)
  *A61B 17/86* (2006.01)
  *A61B 17/88* (2006.01)

(52) U.S. Cl.
  CPC ........ *A61B 17/863* (2013.01); *A61B 17/8897* (2013.01); *A61B 17/152* (2013.01); *A61B 17/1725* (2013.01); *A61B 17/1728* (2013.01); *A61B 17/1739* (2013.01); *A61B 2017/565* (2013.01)

(58) Field of Classification Search
  CPC ....... A61B 17/152; A61B 17/16; A61B 17/17; A61B 17/1725; A61B 17/1728; A61B 17/1739; A61B 17/1782; A61B 2017/565; A61B 2090/062
  USPC .......................................................... 606/87
  See application file for complete search history.

(56) References Cited

U.S. PATENT DOCUMENTS

| | | | |
|---|---|---|---|
| 7,749,278 | B2 | 7/2010 | Frederick et al. |
| 8,021,367 | B2 | 9/2011 | Bourke et al. |
| 8,425,554 | B2 | 4/2013 | Denove et al. |
| 8,545,501 | B2 | 10/2013 | Wong |
| D695,402 | S | 12/2013 | Dacosta et al. |
| 8,828,063 | B2 | 9/2014 | Blitz et al. |
| D720,456 | S | 12/2014 | Dacosta et al. |
| 8,992,532 | B2 | 3/2015 | Wong |
| 9,044,250 | B2 | 6/2015 | Olsen et al. |
| 9,060,822 | B2 | 6/2015 | Lewis et al. |
| 9,107,715 | B2 | 8/2015 | Blitz et al. |
| 9,204,874 | B2 | 12/2015 | Denove et al. |
| 9,814,474 | B2 | 11/2017 | Montoya et al. |
| 9,907,558 | B2 | 3/2018 | Fallin et al. |
| 9,918,854 | B2 | 3/2018 | Bonin, Jr. et al. |
| 9,949,744 | B2 | 4/2018 | McCormick |
| 10,039,559 | B2 | 8/2018 | Awtrey et al. |
| 10,045,862 | B2 | 8/2018 | Wong |
| 10,245,086 | B2 | 4/2019 | Treace et al. |
| 10,342,529 | B2 | 7/2019 | Fallin et al. |
| D860,456 | S | 9/2019 | Buchanan et al. |
| 10,463,407 | B2 | 11/2019 | Taylor et al. |
| 10,512,470 | B1 | 12/2019 | Bays et al. |
| 10,524,808 | B1 | 1/2020 | Hissong et al. |
| 10,575,862 | B2 | 3/2020 | Bays et al. |
| 10,582,936 | B1 | 3/2020 | Hissong et al. |
| 10,610,241 | B2 | 4/2020 | Wagner et al. |
| 10,646,263 | B2 | 5/2020 | Lamm et al. |
| 10,653,432 | B2 | 5/2020 | Luttrell et al. |
| 10,653,465 | B2 | 5/2020 | Blacklidge |
| 10,653,467 | B2 | 5/2020 | Brumfield et al. |
| 10,682,168 | B2 | 6/2020 | Kay et al. |
| 10,736,641 | B2 | 8/2020 | Fallin et al. |
| 10,736,645 | B2 | 8/2020 | McCormick |
| 10,786,291 | B2 | 9/2020 | Weiner et al. |
| 10,881,436 | B2 | 1/2021 | Muller et al. |
| 10,888,335 | B2 | 1/2021 | Dayton et al. |
| 10,888,340 | B2 | 1/2021 | Awtrey et al. |
| 10,888,365 | B2 | 1/2021 | Tyber et al. |
| 11,000,298 | B1 | 5/2021 | Graziano |
| 11,007,068 | B2 | 5/2021 | Wong |
| 11,033,304 | B2 | 6/2021 | Blacklidge |
| 11,039,873 | B2 | 6/2021 | Santrock et al. |
| 11,051,831 | B2 | 7/2021 | Luttrell et al. |
| 11,076,863 | B1 | 8/2021 | Bays et al. |
| 11,147,590 | B2 | 10/2021 | Dayton et al. |
| 11,229,443 | B2 | 1/2022 | Wong et al. |
| 11,246,588 | B2 | 2/2022 | Maclure et al. |
| 11,304,735 | B2 | 4/2022 | Sayger et al. |
| 11,317,954 | B2 | 5/2022 | Nachtrab et al. |
| 11,324,497 | B2 | 5/2022 | Isch et al. |
| 2008/0015605 | A1* | 1/2008 | Collazo ............... A61B 17/157 606/87 |
| 2008/0294170 | A1* | 11/2008 | O'Brien ............... A61B 17/152 606/87 |
| 2011/0213376 | A1* | 9/2011 | Maxson ............... A61B 17/152 606/88 |
| 2013/0231668 | A1* | 9/2013 | Olsen .................... A61B 17/151 606/87 |
| 2013/0296872 | A1* | 11/2013 | Davison ............... A61B 17/152 606/87 |
| 2016/0199076 | A1* | 7/2016 | Fallin ................. A61B 17/1739 606/301 |
| 2016/0324532 | A1 | 11/2016 | Montoya et al. |
| 2017/0079701 | A1 | 3/2017 | Geldwert |
| 2017/0164989 | A1 | 6/2017 | Weiner et al. |
| 2018/0110530 | A1 | 4/2018 | Wagner et al. |
| 2018/0250024 | A1 | 9/2018 | Woodard et al. |
| 2019/0125418 | A1 | 5/2019 | Muller et al. |
| 2019/0175237 | A1 | 6/2019 | Treace et al. |
| 2019/0307495 | A1 | 10/2019 | Geldwert |
| 2020/0046412 | A1 | 2/2020 | Nachtrab et al. |
| 2020/0054374 | A1 | 2/2020 | Schumacher et al. |
| 2020/0060697 | A1 | 2/2020 | Nachtrab et al. |
| 2020/0060739 | A1 | 2/2020 | Nachtrab et al. |
| 2020/0129304 | A1 | 4/2020 | Korman et al. |
| 2020/0170655 | A1 | 6/2020 | Zakhary et al. |
| 2020/0205844 | A1 | 7/2020 | Hissong et al. |
| 2020/0229828 | A1 | 7/2020 | Wagner et al. |
| 2020/0261128 | A1 | 8/2020 | Kay et al. |
| 2020/0275959 | A1 | 9/2020 | Brumfield et al. |
| 2021/0045756 | A1 | 2/2021 | Zakhary et al. |
| 2021/0077120 | A1 | 3/2021 | Hatch et al. |
| 2021/0077162 | A1 | 3/2021 | Muller et al. |
| 2021/0085346 | A1 | 3/2021 | Awtrey et al. |
| 2021/0106372 | A1 | 4/2021 | Tyber et al. |
| 2021/0228381 | A1 | 7/2021 | Wong |
| 2021/0259716 | A1 | 8/2021 | Woodard et al. |
| 2021/0267649 | A1 | 9/2021 | Blacklidge |
| 2021/0282823 | A1 | 9/2021 | Day et al. |
| 2021/0290251 | A1 | 9/2021 | Luttrell et al. |
| 2021/0361294 | A1 | 11/2021 | Bays et al. |
| 2022/0008106 | A1 | 1/2022 | Ellington |
| 2022/0039816 | A1 | 2/2022 | Bruse |

FOREIGN PATENT DOCUMENTS

| | | |
|---|---|---|
| WO | 2020172451 A1 | 8/2020 |
| WO | 2021126326 A1 | 6/2021 |
| WO | 2021158738 A1 | 8/2021 |
| WO | 2021162805 A1 | 8/2021 |
| WO | 20211167992 A1 | 8/2021 |
| WO | 2021173931 A1 | 9/2021 |
| WO | 2021206905 A1 | 10/2021 |
| WO | 2021211249 A1 | 10/2021 |
| WO | 2021212131 A1 | 10/2021 |

* cited by examiner

METHOD, SURGICAL APPARATUS, AND SURGICAL IMPLANT FOR MINIMALLY INVASIVE SURGICAL PROCEDURES

CROSS-REFERENCE TO RELATED APPLICATION

The present application is a 371 application of international PCT/US2020/64002 filed on Dec. 9, 2020, which claims priority on U.S. Provisional Patent Application Ser. No. 62/947,376, filed Dec. 12, 2019 and entitled MIS Chevron Surgical Guide and Processes for Using the Same, the entirety of both of which is hereby incorporated herein by reference.

BACKGROUND OF THE INVENTION

1. Field of the Invention

The present invention relates in general to the field of surgery. More particularly, the present invention relates to an orthopedic implant, surgical instruments for use and delivery of the implant, surgical instruments for creation of an osteotomy, and the surgical technique used with these items. Specifically, a preferred embodiment of the present invention relates to methods and instruments used for minimally invasive surgery.

2. Discussion of the Related Art

An osteotomy is a surgical procedure that involves cutting, reshaping, or removing bone. Osteotomies are usually performed to correct a deformity in the bone. One common deformity that can be repaired by surgery is hallux valgus, also known as a bunion. Hallux valgus is a foot deformity that causes functional disability and pain and involves misalignment of the first metatarsal and phalanx.

Surgical correction frequently involves cutting bone, realigning or shifting the bones to the proper anatomical configuration, and then fixing the bones in the new positions such that they heal. Fixation of the bones can occur with the use of orthopedic screws, shape memory implants, or plates and screws. The surgery frequently requires incisions in the skin and soft tissues and then subsequent cutting and drilling of bone. Many conventional systems for surgery of this type require extensive dissection of soft tissue such that the physician can see the underlying bone. Extensive dissection such as this can limit or damage blood flow to the affected area and slow healing. Extensive dissection of soft tissue also risks penetrating the area around a joint, potentially permanently compromising proper joint motion. Soft tissue dissection can also damage nerves, increase swelling, or increase post-surgical pain.

Therefore, during surgery of this type, it is frequently an objective of the surgeon to avoid unnecessary disruption of tissue. This can be accomplished by both careful surgical techniques, as well as specially designed instruments and implants that minimize unnecessary tissue disruption. In particular, a precision guide can assist a physician in accomplishing surgery with minimal tissue dissection. A medical device system that is designed to assist the surgeon in minimizing unnecessary disruption of tissue can be described as "minimally invasive surgery".

Accordingly, what is needed is a medical device system that includes instruments, implants, and a surgical technique that work together to avoid unnecessary disruption of tissue and producing a successful surgical outcome. What is further needed are medical devices and processes that solves the problem outlined above associated with large incisions and variable surgical results. What is further needed is an apparatus and method of use resulting in minimal soft tissue disruption and providing specific guided steps for the surgery.

SUMMARY AND OBJECTS OF THE INVENTION

In accordance with a first aspect of the invention, an apparatus is provided that includes a precision cutting guide for creating an osteotomy. The guide includes a main body shaped to conform to an outside surface of a foot of a patient having at least one opening, a cutting guide insert with a chevron-shaped cutting slot capable of receiving a cutting instrument, at least one adjustment screw that is movable relative to the main body to secure the main body to the foot of the patient, and at least one guide wire insertable into the at least one opening. The cutting guide insert may be radiopaque. Additionally, the main body may have at least one alignment slot formed in the main body that is configured to allow the precision cutting guide to be aligned with the foot of the patient. Similarly, the main body may have at least one notch formed along the perimeter of the main body for aligning the main body relative to the foot of the patient. The main body may also have at least one curved edge formed in the body. The curved edge may be used as a guide for a physician to make a curvilinear incision. Further still, the guide may include a targeting knob that extends from the main body. At least one hole may be formed in the targeting knob. For instance, the targeting knob may have a center targeting hold, as well as at lease one additional adjustment holes located proximate to the center targeting hole. Additionally, the guide may include a guide tube slot that is formed in the main body that is substantially perpendicular to the cutting slot.

According to another aspect of the present invention, a method of performing a medical procedure is provided. The method may include the steps of aligning a precision cutting guide relative to the foot of the patient, securing the precision cutting guide relative to the foot, making an incision in the foot along an edge of the main body, inserting at least one retractor into the incision, cutting a portion of a bone into a first bone piece and a second bone piece, adjusting the location of the first bone piece relative to the second bone piece, and securing the first bone piece to the second bone piece. Additionally, the method includes the steps of drawing a first line along a centerline of a first metatarsal of the foot, drawing a second line substantially perpendicular to the first line, aligning at least one of the first line and the second line with at least one slot or notch. Further still, the method may include the step of tightening at least one adjustment screw that is rotatably attached to the main body to secure the main body to the foot. Further still, the method may include the steps of securing a targeting guide to the main body and inserting at least one guide wire through the targeting guide, the main body, and into a first metatarsal of the foot. Additionally, the method may include the steps of rotating the main body about the at least one guide wire from a first position to a second position and cutting an incision in the foot about the at least one edge. Thereafter, at least one retractor may be inserted into the incision, after which the main body may be rotated about the at least one guide wire from the second position back to the first position. Next, a screw guide may be inserted into a guide tube slot formed in the main body, after which a guide wire may be inserted through the screw guide. Thereafter, the first metatarsal of the patient's foot can be cut through a cutting guide slot formed in the main body to create a first bone piece and a second bone piece. After that, the first bone piece may be adjusted relative to the second bone piece, a hole can be drilled into the bone using the guide wire as a guide, and an implant can be screwed in to secure the first bone piece to the second bone piece. Next, any remaining guide wires can be removed, and the incision can be closed. Furthermore, x-rays or other visual scans may be taken at any point during the procedure to ensure appropriate location of the various components. The desired method creates a step-by-step surgical procedure that helps to ensure the osteotomy and implant are in the correct location for a high success outcome.

According to another aspect of the present invention, a kit may be provided. The surgical kit provides a receptacle for holding the different components of the minimally invasive surgical system and keeps each component secure and sterile until the time of surgery. The kit may include a precision cutting guide, at least one screw rotatably connected to the precision cutting guide, at least one guide wire, and an implant configured to secure two pieces of bone together. The kit may also include a targeting guide that is configured to be releasably secured to the main body about a targeting knob having a plurality of openings formed therein. The kit may also include at least one retractor configured to retract soft tissue in the foot. Further still, the kit may include a screw guide that is configured to be inserted into a guide tube slot formed in the main body. Further yet, the kit may include a scalpel, a screwdriver, and a drill bit. Each of the screwdriver, drill bit, and screw guard may have a cannula formed therein dimensioned to accommodate the at least one guide wire. The kit may consist of single-use instruments and all necessary implants required to perform a surgical correction of mild to moderate hallux valgus, or similar surgical procedure.

According to another aspect, the invention includes each of the following plus their combination: a precision cutting guide, a targeting guide, a screw guide, a screwdriver, one or more orthopedic implants, a drill bit with countersink, one or more tissue retractors, one or more guide wires, and a kit or kits for maintaining the sterility of the components.

The precision cutting guide is designed to conform to the anatomy of a patient. It provides a guide for a physician to create an osteotomy by guiding a bone saw blade to the proper location and at the proper angles. The precision cutting guide has numerous alignment features such as holes and notches to assist the physician with positioning the guide in the proper location for a successful osteotomy of bone. The precision cutting guide also has a guide tube slot that allows the physician to direct a guide wire directly to the location needed for proper fixation.

The targeting guide is designed to help align the precision cutting guide such that is positioned properly over a bone under the skin. The targeting guide fits over the precision cutting guide, such that the targeting guide is perpendicular to the cutting slot on the precision cutting guide. The targeting guide features a pointer that can be directed at a specific anatomic location to assist the physician. The screw guide allows the physician to determine the correct length of implant to use for fixation, and then guide an implant into the correct spot to fixate two bones. The screwdriver is cable of fitting over the guide wire while driving an implant into bone.

The orthopedic implant can consist of different types of fixation implants, such as a bone screw, bone pin, surgical staple, or orthopedic plate with screws. In this system, the orthopedic implant consists of a cannulated orthopedic screw. The precision cutting guide provides a mechanism for targeting the location of the orthopedic implant, such that the physician can rely on proper placement of the implant with no unnecessary soft tissue dissection.

The drill bit with countersink permits drilling of a pilot hole for the implant, as well cutting flutes to create a countersink area in bone so that the implant does not project above the surface after installation. The tissue retractors are designed to restrain soft tissue while making the osteotomy and allow access to bone. One or more guide wires can be smooth-shafted or threaded and can have one end pointed or both ends pointed. The purpose of the guide wires is to anchor the precision cutting guide to the patient's anatomy with minimal soft tissue disruption, so that an osteotomy can be created, and the implant targeted to the proper location.

The combination of the kit and a surgical technique that results in minimal tissue disruption (also referred to as minimally invasive) and highly reproducible and accurate correction to the hallux valgus condition. The reduces the chance of complications, scarring and pain. A minimally invasive precision surgical cutting guide instrument that has the following features: the main body is clear, so that physicians can see the underlying bone and tissue; the radiopaque cutting guide insert allows the physician to see the exact location where a bone osteotomy, or corrective cut in bone, will occur; precise alignment features that ensure the osteotomy is performed in the correct location, the osteotomy is centered on the bone, and a fixation implant can be directed to the proper location; adjustment holes that allow the physician to reposition the cutting guide without drilling additional guide wires into bone; a targeting guide instrument that ensures the osteotomy is perpendicular to the metatarsal bone that is being surgically corrected. The present invention may be is unique to foot and ankle surgery, or it similarly could be used for other surgical procedures.

These, and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
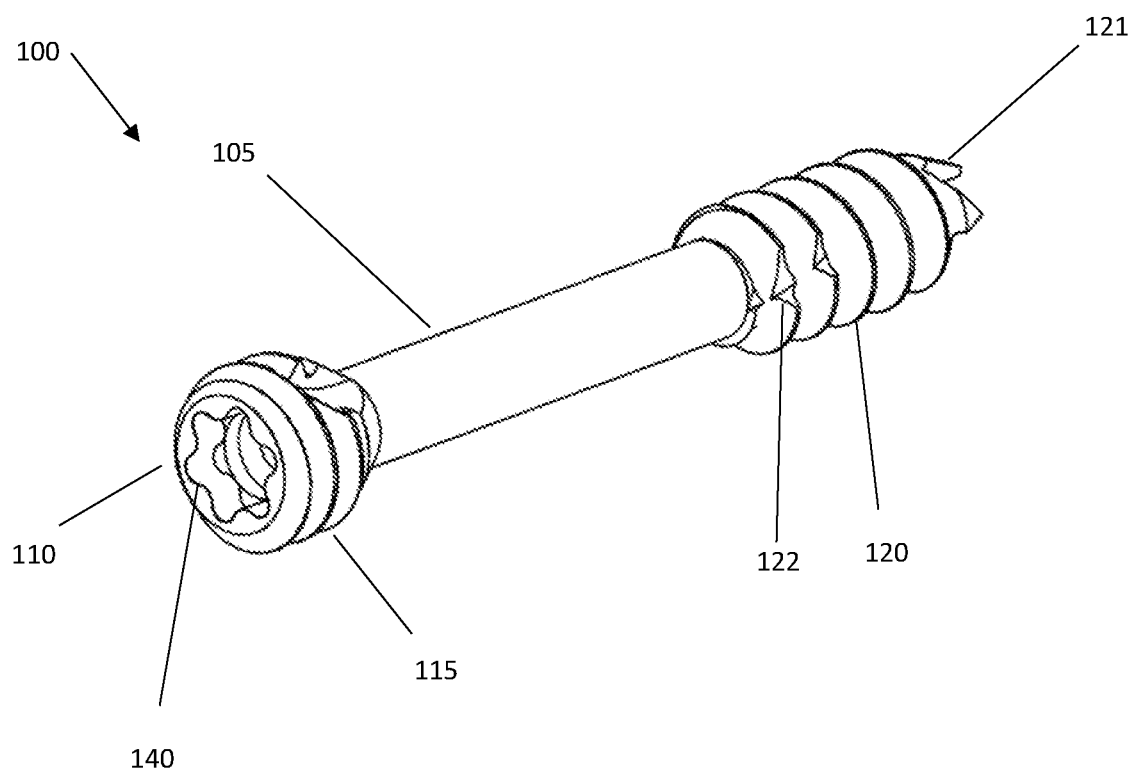
FIG. 1 is an isometric perspective view of an orthopedic implant.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected, attached, or terms similar thereto are often used. They are not limited to direct connection but include connection through other elements where such connection is recognized as being equivalent by those skilled in the art.

DETAILED DESCRIPTION OF PREFERRED EMBODIMENTS

The present invention and the various features and advantageous details thereof are explained more fully with reference to the non-limiting embodiments described in detail in the following description. Initially, a variety of tools will be described, after which use of the tools together will be described to perform the desired medical procedure. Preferably, the described system can be used to streamline and simplify minimally invasive surgical procedures. Additionally, the described system preferably results in better cosmetic results, such as less scarring, decreased trauma to the soft tissues, less damage to blood supply, faster healing, less time in the operating room for the patient and physicians, less post-operative pain, swelling, and complications, and/or quicker recovery time and earlier return to activities. While the description below will primarily be in relation to surgical procedures designed to correct issues relating to hallux valgus/bunions, the present invention could similarly be used to correct other issues in a patient's feet, ankles, and elsewhere on the body.

Figure 2:
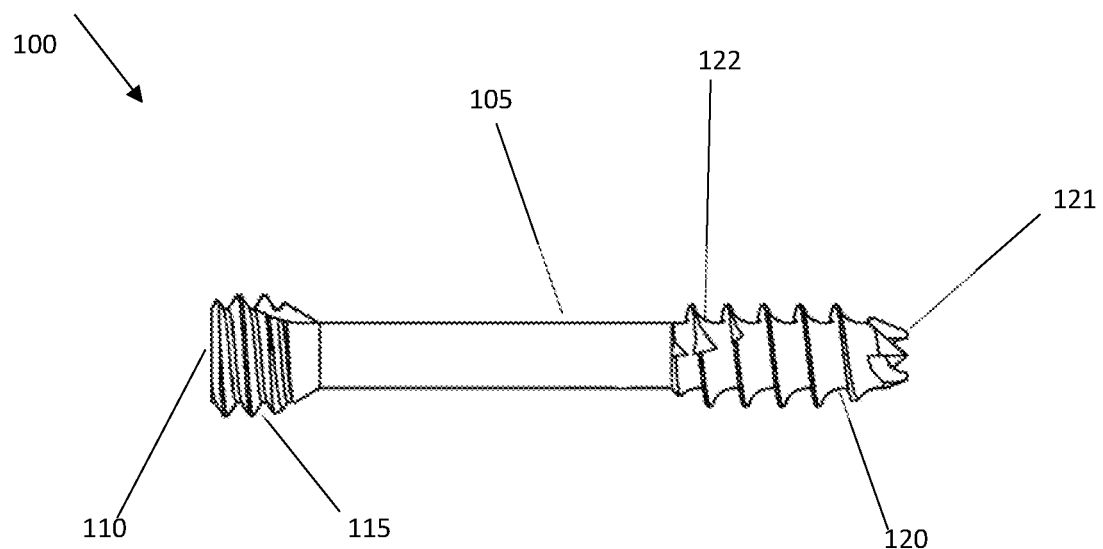
FIG. 2 is a side elevation view of the orthopedic implant of FIG. 1.
Figure 3:
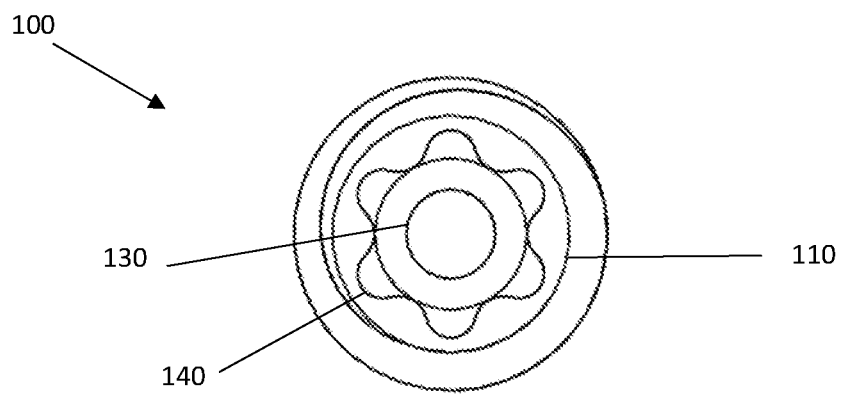
FIG. 3 is an end elevation view of the orthopedic implant of FIGS. 1 and 2.

FIGS. 1-3 are perspective, side view, and end views respectively, of an orthopedic implant 100 suitable for fixating two bones after an osteotomy and corrective surgery. In one embodiment of the present invention, the implant 100 consists of a cannulated orthopedic screw. The illustrated implant 100 consists of a shaft 105, a head 110, upper threads 115, and distal threads 120. The implant 100 can be manufactured of metal, plastic, or any other suitable material depending on the objectives of the designer and the purpose of use of the implant 100. The shaft 105 has an inner cannula 130 that extends from the head 110 to the cutting tip 121 along the entire length of the implant 100. The diameter of the cannula 130 is sized such that a guide wire 650, described below, passes through the cannula 130. The head 110 contains upper threads 115, which anchor in one bone requiring fixation. The distal threads 120 anchors in a second bone to create fixation. The thread pitch and diameter of the upper threads 115 and the distal threaded section 120 can be different, such that a compressive force is created between two bones upon the use of the implant 100. The distal threads 120 contain a cutting tip 121, which can self-cut threads into a bone as the implant 100 is screwed into place. The distal threads 120 also contain reverse cutting threads 122, which allow the implant 100 to be removed from bone if desired. The head 110 also contains a screwdriver receptacle 140. The receptacle 140 is shown in the preferred embodiment to receive a Torx head screwdriver, however any design for mating with a screwdriver could suffice. Although the implant is shown as a screw, other implants may be used to achieve the same goal, including pins, staples, plates, and any other fastener mechanism known to those having ordinary skill in the art. Additionally, the implant 100 may be a similar screw as shown, but having different lengths depending on the size and shape of the patient's foot.

Figure 4:
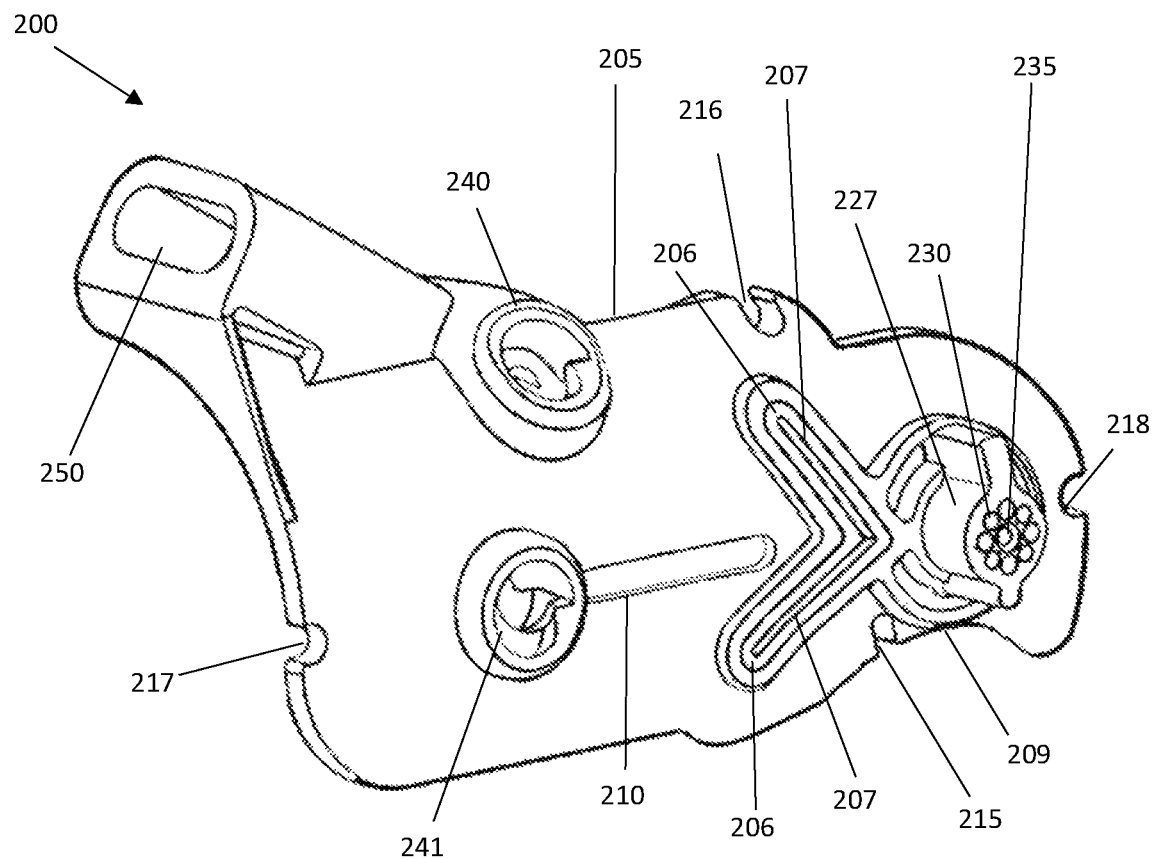
FIG. 4 is an isometric perspective view of a precision cutting guide.
Figure 5:
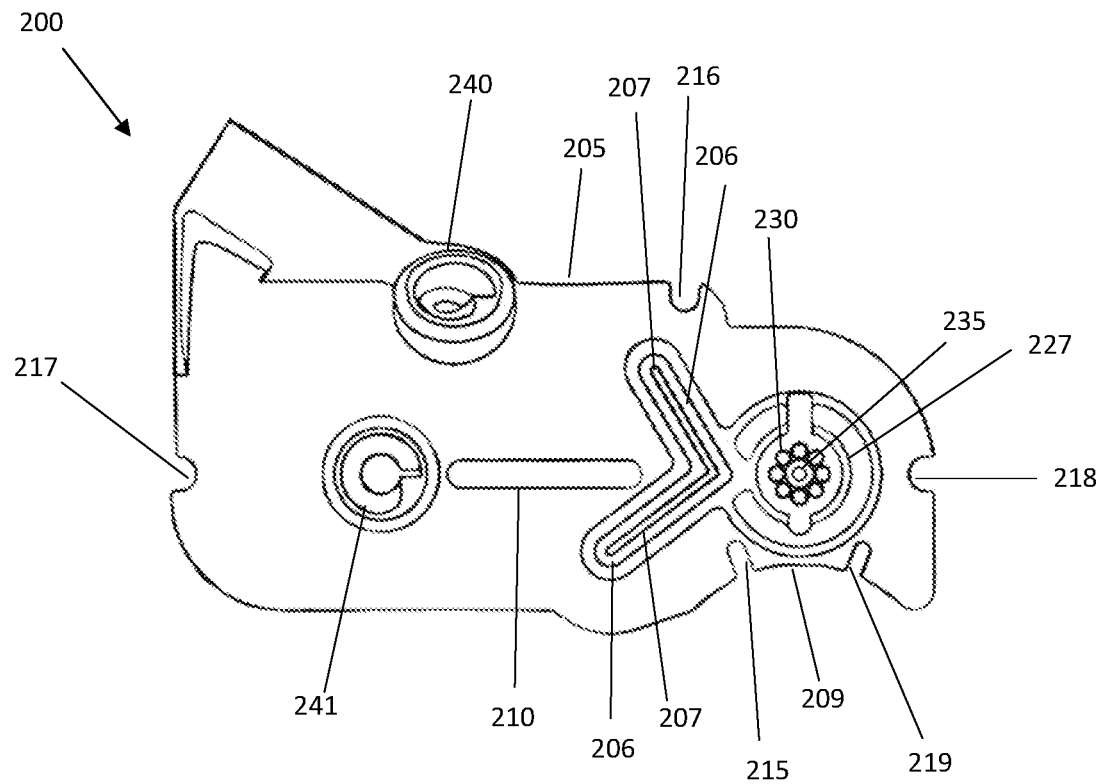
FIG. 5 is a side elevation view of the precision cutting guide of FIG. 4.
Figure 6:
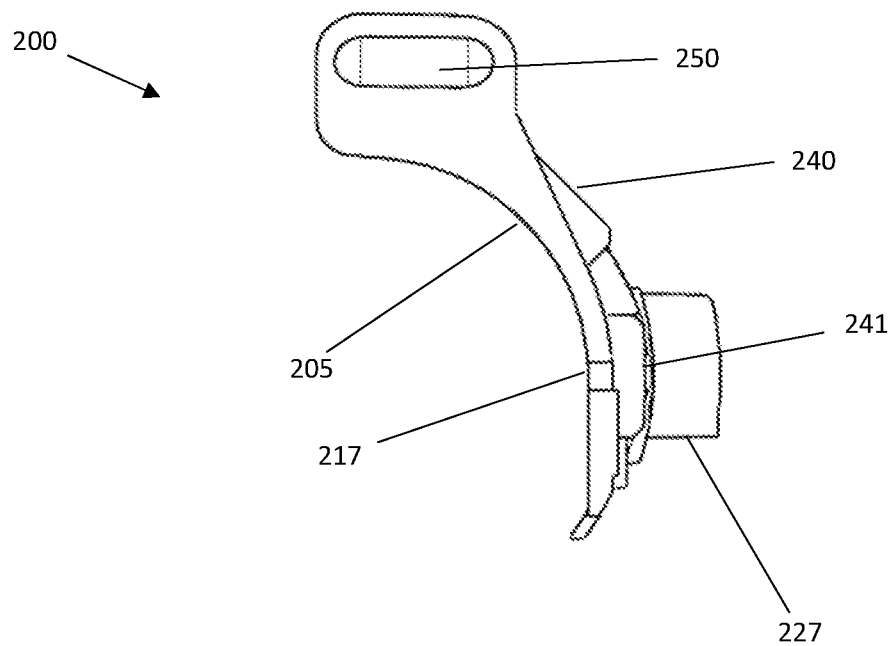
FIG. 6 is an end elevation view of the precision cutting guide of FIGS. 4 and 5.

Next, FIGS. 4-6 are perspective, side view, and end views respectively, of one embodiment of a precision cutting guide 200. The precision cutting guide 200 is shown designed for the left foot of a patient, but all description below applies for a right foot where a mirror image version of guide 200 would be used. The precision cutting guide 200 consists of a main body 205, which conforms to the anatomy of the left foot. In this embodiment, the shape of the main body 205 is curved in multiple planes to best conform to the soft tissue surrounding a patient's first metatarsal. The main body 205 can be made of plastic, metal, or any other suitable material depending on a number of factors, including whether the precision cutting guide 200 is intended to be disposable, or reusable, the desire of the user, and the like. Biocompatible ink can be used on the main body 205 to highlight measurements or features to a surgeon. For example, the letter "L" signifying left foot could be printed on the precision cutting guide 200.

The main body 205 has an insert situated in it. For instance, a cutting guide insert 206 is embedded in a cavity in the main body 205. In this embodiment, the cutting guide insert 206 is over molded into the main body 205, but any means of attachment would suffice. For example, the cutting guide insert 206 could be glued, press fit, welded, or attached in another way to main body 205. The cutting guide insert 206 can be made from a different material than main body 205, or it could be made of the same material. In this embodiment, the main body 205 is made from conventional injection molded plastic, whereas cutting guide insert 206 is made from radiopaque injection molded plastic. In this way, when a physician uses the precision guide 200, the cutting guide insert 206 is visible in fluoroscopy. A cutting slot 207 is a chevron-shaped (V-shaped) pathway that permits an orthopedic cutting instrument, such as saw or bur, to make a cut in bone. Of course, the cutting slot 207 could take any number of different shapes depending on thus surgical procedure being performed, and the preferences of the physician. When the precision cutting guide 200 is positioned on a patient's foot, and fluoroscopy is used, the cutting slot 207 would be easily visible in the center of the radiopaque cutting guide insert 206, ensuring that a physician user would cut bone in the correct spot.

The precision cutting guide 200 includes several alignment features. First, an alignment slot 210 is a straight slot in the main body 205 that allows viewing of tissue under the precision cutting guide 200. An upper alignment notch 216 and horizontal notches 217 and 218 are notches on the perimeter of the main body 205 that can be used by a physician to align the precision cutting guide 200 properly on a patient's foot as will further be described below. A line drawn through horizontal notches 217 and 218 would pass through alignment slot 210.

The precision cutting guide 200 also has two lower notches 215 and 219, and an edge 209, located on the bottom perimeter of the precision cutting guide 200. The edge 209 is a surface that a physician can use to guide a scalpel or cutting device precisely along a curvilinear path. Of course, the edge 209 could similarly be a straight edge or an edge having a different curvilinear path. The curvilinear perimeter distance between the two lower notches 215, 219 along edge 209 can be a known distance. In this embodiment, that distance between the two lower notches 215, 219 tracing along edge 209 is one centimeter. In this way, these three features, 215, 219, and 209 allow the physician to create a one-centimeter guided curvilinear tissue incision with a scalpel.

The precision cutting guide 200 has multiple threaded locations for alignment screws. First, an upper alignment hole 240 is a threaded hole in the main body 205 for accepting an alignment screw 300. Similarly, a lower alignment hole 241 is a threaded hole in the main body 205, for accepting another alignment screw 300. Any number of alignment screws can be used, but in this embodiment only two are needed. Alignment holes 240 and 241 are positioned on main body 205 such that they are not coplanar, allowing for better stabilization when the alignment screws 300 are inserted into the holes 240 and 241.

The precision cutting guide 200 may also have a guide tube slot 250 that is situated on the main body 205 that is designed such that a screw guide 450 fits into the guide tube slot 250 and can be moved from side to side. This allows the screw guide 450 to be aimed at a precise location by the physician.

Further still, the precision cutting guide 200 may also include a targeting knob 227 that extends from the main body 205. The targeting knob 227 is designed such that a targeting guide 500 described below will snugly fit over targeting knob 227 and be secured thereto. The end of targeting knob 227 contains numerous holes. For instance, as shown a center targeting hole 235 has a diameter large enough for a guide wire 650. Additional adjustment holes 230 may be formed in the targeting knob 227 that surround the center targeting hole 235. There can be any number of adjustment holes 230, but in this embodiment eight adjustment holes are shown. The diameter of each adjustment hole 230 is large enough for a guide wire 650. The center point of each of the adjustment holes 230 is a known distance from center targeting hole 235. For example, the center point of each adjustment hole 230 could be 1 mm from center targeting hole 235 if desired by the designer. The adjustment holes 230 allow a physician to reposition the precision targeting guide 200 in small incremental amounts to achieve proper positioning of the precision targeting guide on the patient's foot without redrilling guide wire 650. This adjustment process will be described in more detail below.

Figure 7:
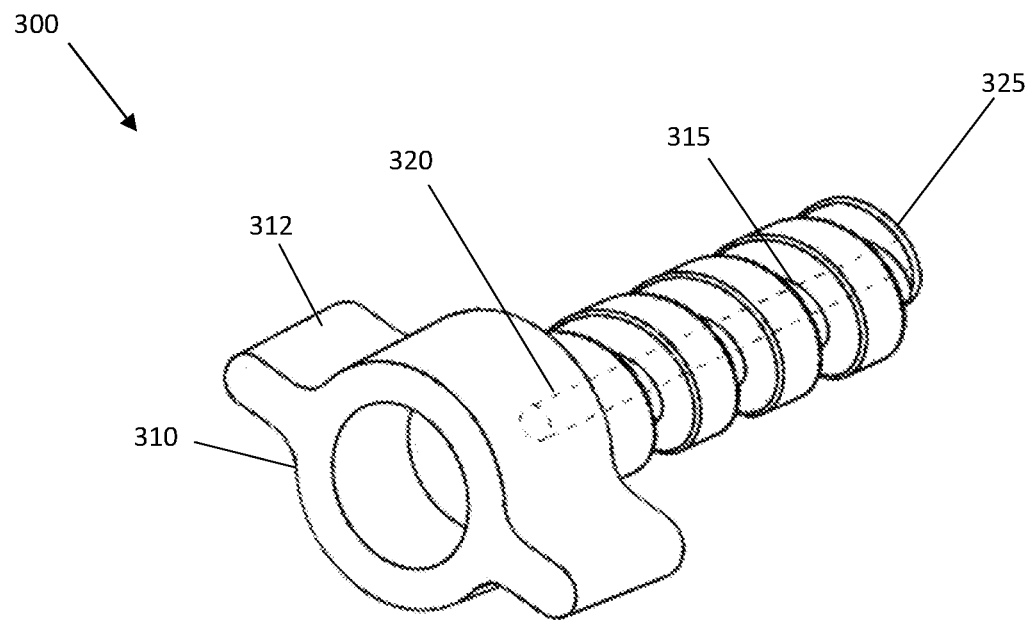
FIG. 7 is an isometric perspective view of an alignment screw.

Moving on, FIG. 7 shows one embodiment of a potential alignment screw 300. The alignment screw 300 can be made of any number of materials, but in this embodiment was designed to be injection-molded plastic. The screw 300 consists of an alignment screw head 310, an alignment screw cannula 320, alignment screw threads 315, and an alignment screw tip 325. The alignment screw head 310 includes flanges 312 such that it can be easily inserted and tightened by a physician. The alignment screw 300 is cannulated from head 310 to tip 325. The diameter of the cannula 320 is such that it will fit over a guide wire 650. The alignment screw threads 315 can be of any pitch and diameter, but in this embodiment the threads 315 show a course thread pattern that advances a large distance for each turn of alignment screw head 310. In addition, the alignment screw threads 315 mate with the threads in the upper and lower alignment holes 240, 241 of the precision cutting guide 200. The alignment screw tip 325 is blunt with no sharp edges and designed to contact soft tissue without damaging soft tissue.

Figure 8:
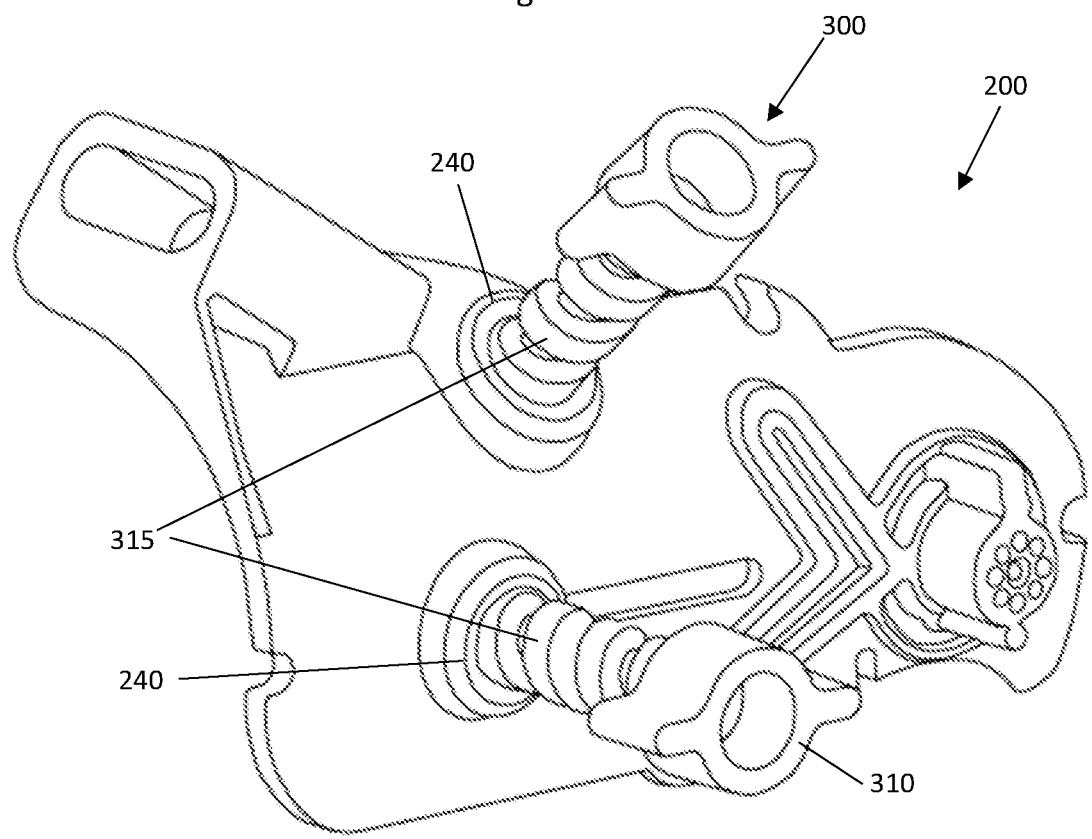
FIG. 8 is an isometric perspective view of the precision cutting guide assembly with alignment screws in place.

FIG. 8 is an illustration of an assembly consisting of the precision cutting guide 200 and two alignment screws 300. The alignment screw threads 315 are engaged with the alignment holes 240, 241 of precision cutting guide 200.

This assembly can be placed on a patient's foot and both alignment screws 300 tightened until they contact soft tissue and stabilize the precision cutting guide 200 relative to the patient's foot.

Figure 9:
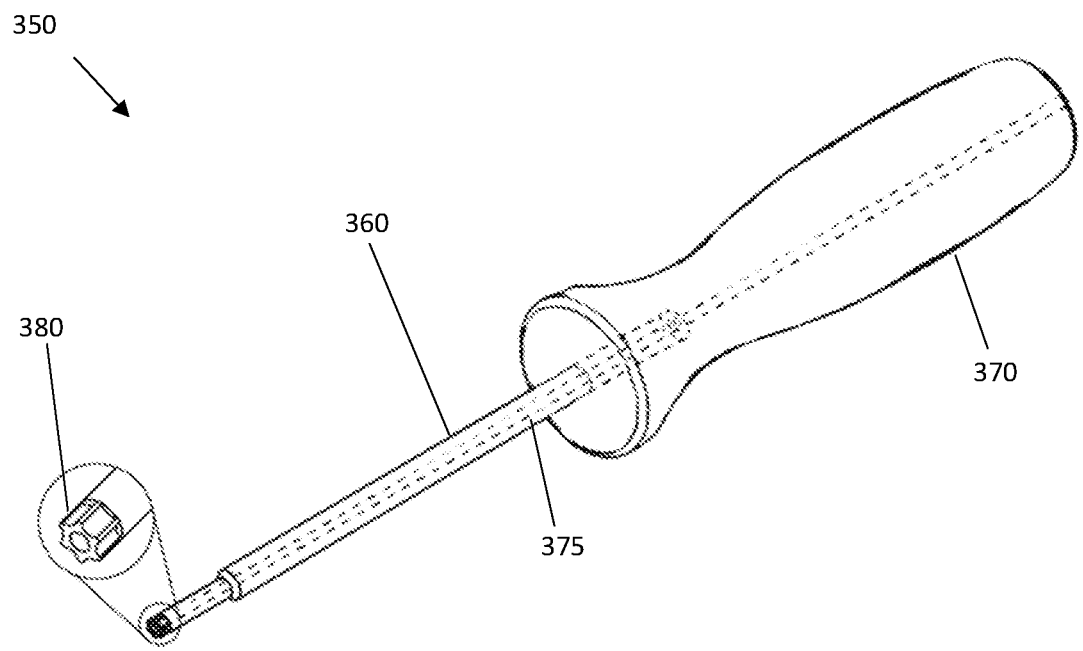
FIG. 9 is an isometric perspective view of a screwdriver with an exploded view of a tip.

A screwdriver 350 used with present invention is shown in FIG. 9. The screwdriver 350 consists of two pieces: a screwdriver shaft 360 and a screwdriver handle 370. In the illustrated embodiment, the screwdriver shaft 360 can be made of metal and over molded with a plastic screwdriver handle 370. However, one familiar with the art can see that screwdriver 350 can be a single piece, of any suitable material, if desired, or a multiple piece screwdriver made of any desired material or materials. The screwdriver handle 370 can be a solid block, or it can be partially hollowed to reduce weight. A screwdriver cannula 375 extends from screwdriver tip 380 to the end of handle 370. The cannula 375 is large enough for a guide wire 650. The screwdriver tip 380 is designed to mate with screwdriver receptacle 140 on the implant 100. In this embodiment the screwdriver tip 380 is shown as a Torx design, although any other type of screwdriver tip may be used.

Figure 10:
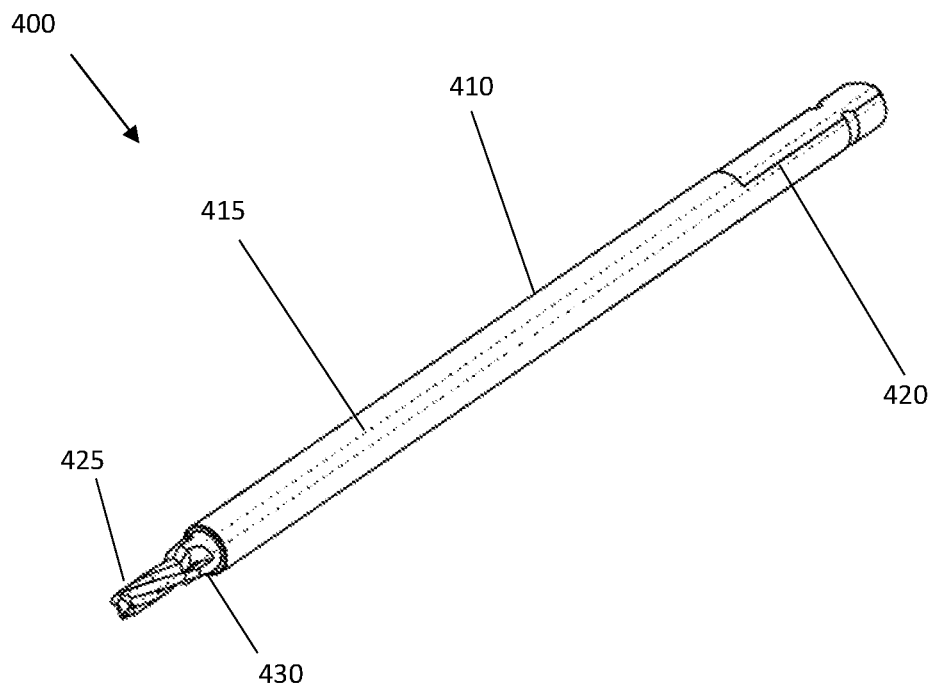
FIG. 10 is an isometric perspective view of a drill bit.
Figure 11:
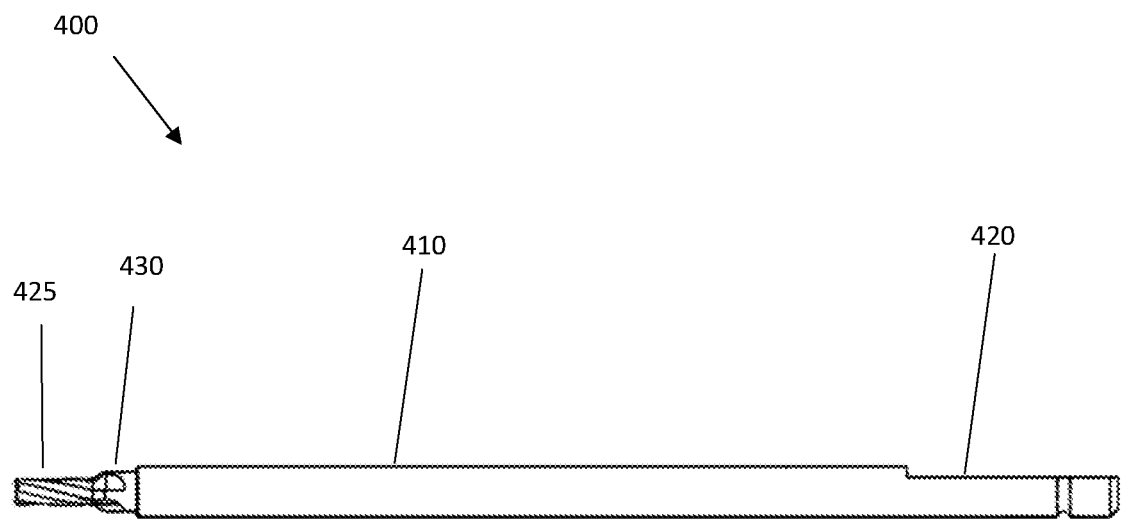
FIG. 11 is a side elevation view of the drill bit of FIG. 10.

Additionally, FIGS. 10 and 11 illustrate a drill bit 400. The drill bit 400 consists of a drill bit body 410, a drill bit quick connect 420, and two sets of cutting flutes 425 and 430. The drill bit 400 is cannulated from end to end with a drill bit cannula 415 having a diameter that is configured to receive a guide wire 650. The drill bit quick connect 420 is a design that fits common surgical drills and can be whatever shape and design is suitable to be compatible with operating room drills. The cutting flute 425 has a diameter that is suitable for an implant 100 distal threads 120. The countersink cutting flute 430 has a larger diameter than the cutting flute 425, and creates an opening for the upper threads 115 on the implant 100, such that the implant head 110 can be inserted deep enough in a bone such that it does not project above the surface of the bone. The length of fluted area on the drill bit 400 depends on whether the implant 100 contains threads with self-cutting design. In this embodiment, the implant 100 distal threads 120 are self-cutting, and therefore the cutting flute 425 does not need to be as long as the implant 100.

Figure 12:
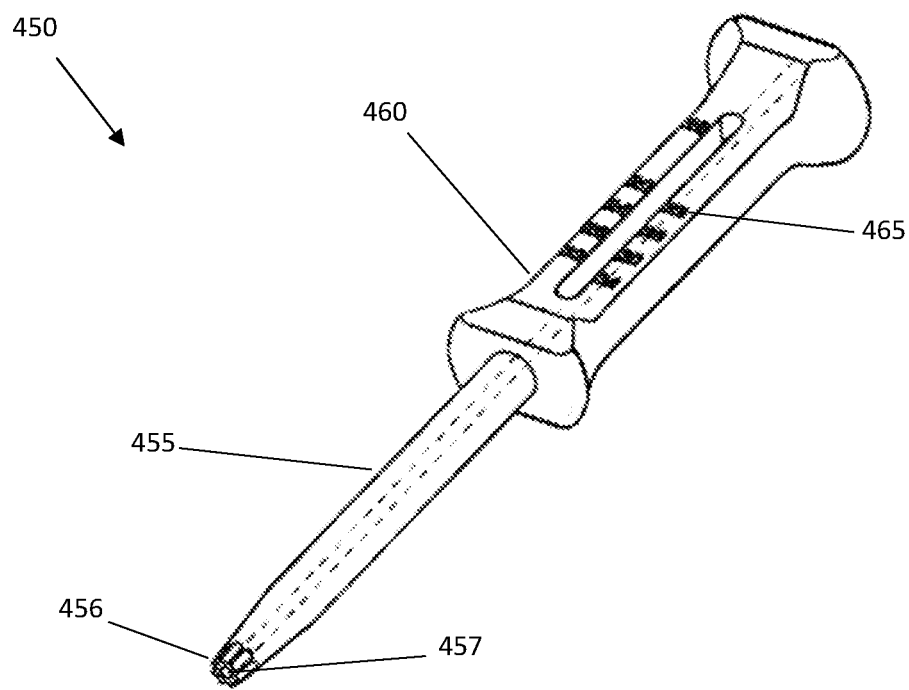
FIG. 12 is an isometric perspective view of a screw guide.

Next, FIG. 12 shows a screw guide 450. The screw guide 450 consists of a tissue protector sleeve 455 and a depth gauge handle 460. The tissue protector sleeve 455 can be made of any material, but in this embodiment is made from metal. A sleeve tip 456 at the end of the tissue protector sleeve 455 has serrated edges, so that it can grip a patient's bone when used in surgery. A cannula 457 extends through the length of the screw guide 450 and is configured to receive a guide wire 650. The depth gauge handle 460 can be printed or embossed with depth gauge measurements 465, which can be used by a physician to determine what length of implant 100 would be needed for a given patient.

Figure 13A:
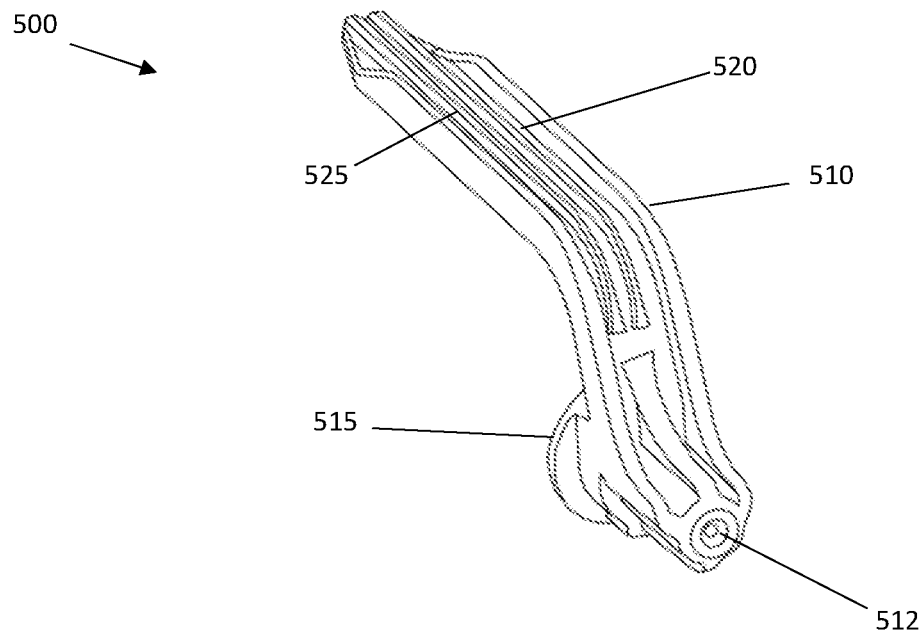
FIG. 13A is an isometric perspective view of a targeting guide.
Figure 13B:
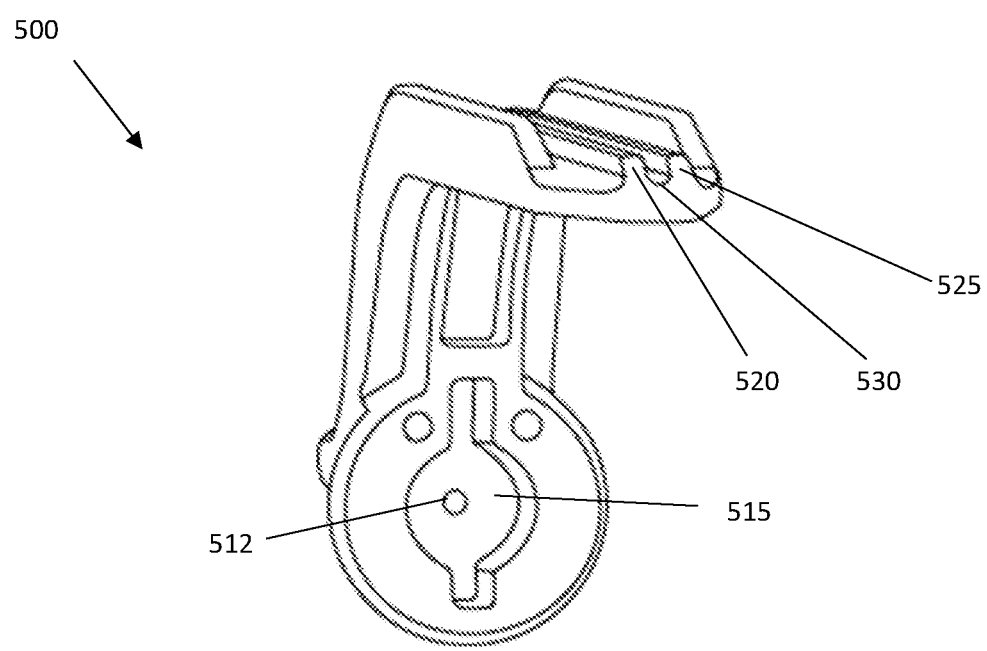
FIG. 13B is a different isometric perspective view of the targeting guide of FIG. 13A.
Figure 14:
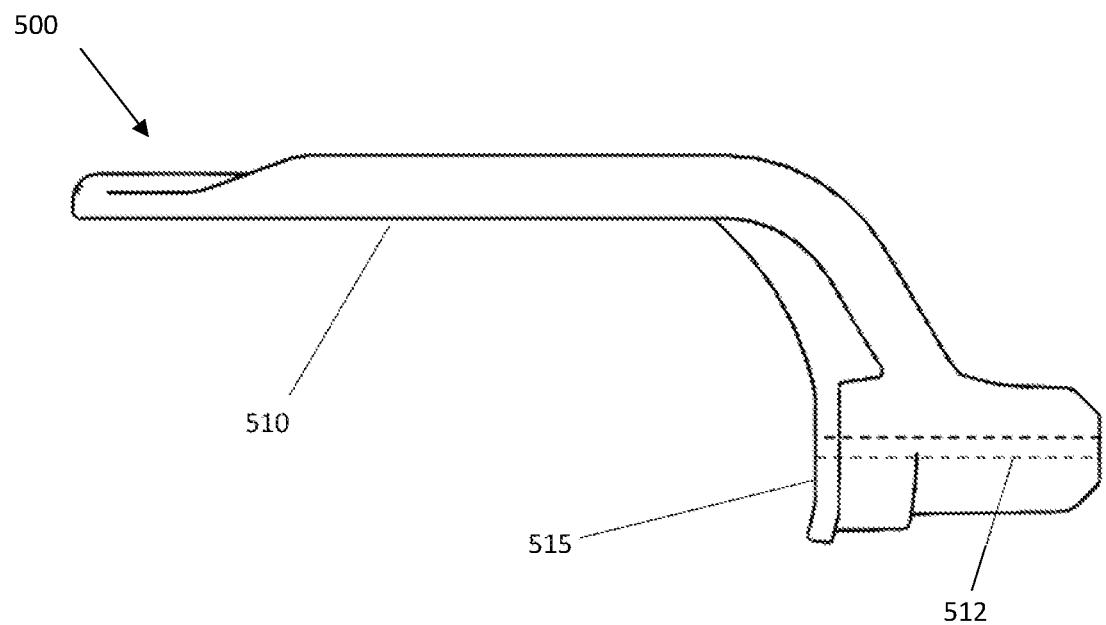
FIG. 14 is a side elevation view of the targeting guide of FIGS. 13A and 13B.
Figure 15:
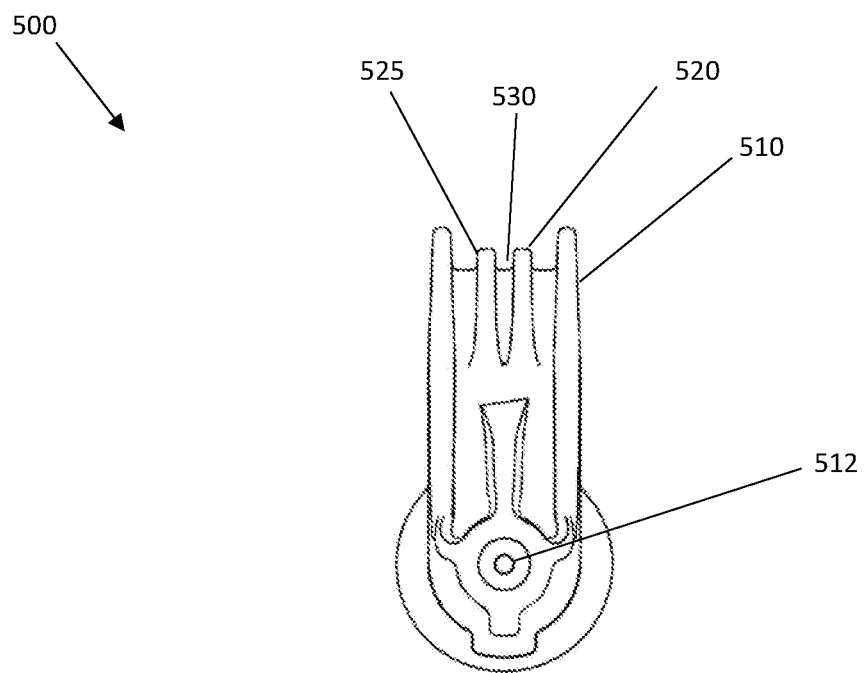
FIG. 15 is an end elevation view of the targeting guide of FIGS. 13A-14.

FIGS. 13A, 13B, 14 and 15 illustrate different views of a targeting guide 500. The targeting guide 500 has a targeting pointer 510. A targeting guide cannula 512 may extend through a portion of the targeting guide 500, where the cannula 512 has a diameter that is configured to receive a guide wire 650. A targeting guide recess 515 may be shaped so that it fits over the targeting knob 227 of the precision cutting guide 200. When the targeting guide recess 515 is slipped over targeting knob 227, it causes the targeting pointer 510 to be oriented perpendicularly to the alignment slot 210 and the cutting guide insert 206 on the precision cutting guide 200. In this embodiment, the targeting guide 500 is made from injection-molded plastic, although it could be made of any other suitable material. The targeting guide 500 can be designed with ribs to improve strength, if desired. In this embodiment, pointer 510 has two ribs along its length. As shown, two ribs 520, 525 are located on the pointer 510 and designed so that a groove 530 is formed between ribs 520 and 525. The width of groove 530 is slightly larger than the diameter of a guide wire 650. In this way, a guide wire 650 can be laid into the groove 530 formed by the ribs 520, 525 and extend from the targeting pointer 510 to a landmark on the patient's body. The targeting pointer 510 can also be designed such that it comes to a point at the end or left blunt as shown in FIG. 13A.

Figure 16:
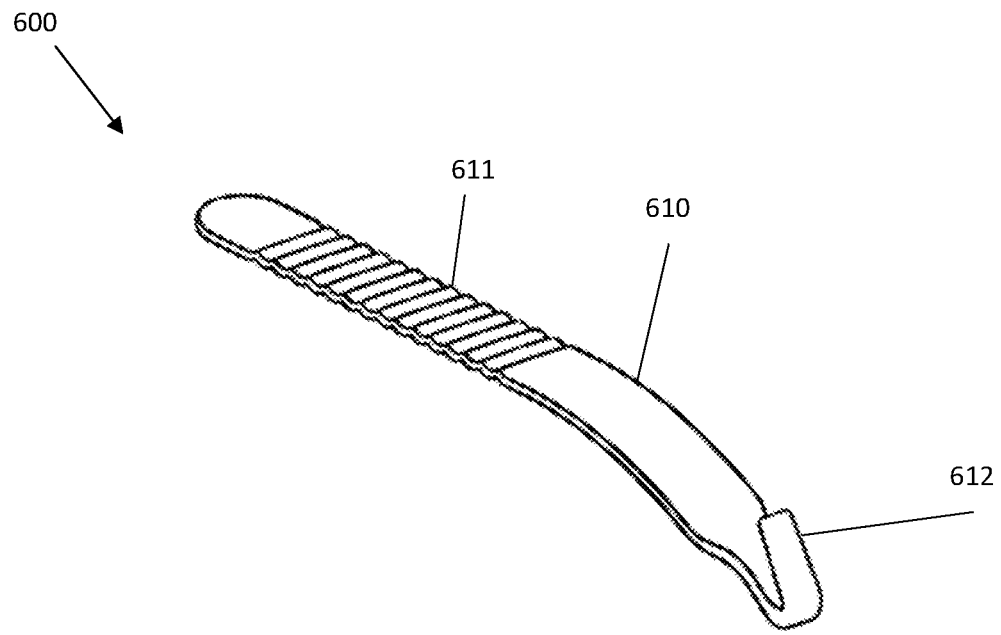
FIG. 16 is an isometric perspective view of a small tissue retractor.
Figure 17:
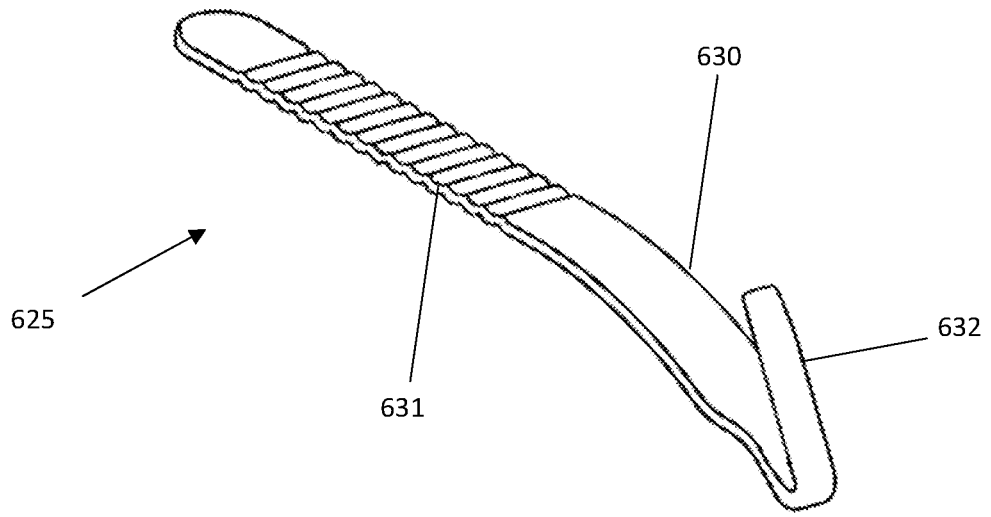
FIG. 17 is an isometric perspective view of a large tissue retractor.

FIG. 16 illustrates a short tissue retractor 600. The retractor 600 consists of a short retractor body 610, a grip 611, and a short tissue hook 612. The purpose of the tissue retractor 600 is to allow the physician user to grab and retract soft tissue around an incision, to expose bone under the tissue. Similarly, FIG. 17 illustrates a long tissue retractor 625. The retractor 625 is similar in design to short tissue retractor 600, except that the long tissue hook 632 is longer than the short tissue hook 612. A long retractor body 630 and a grip 631 make up the body of long tissue retractor 625.

Figure 18:
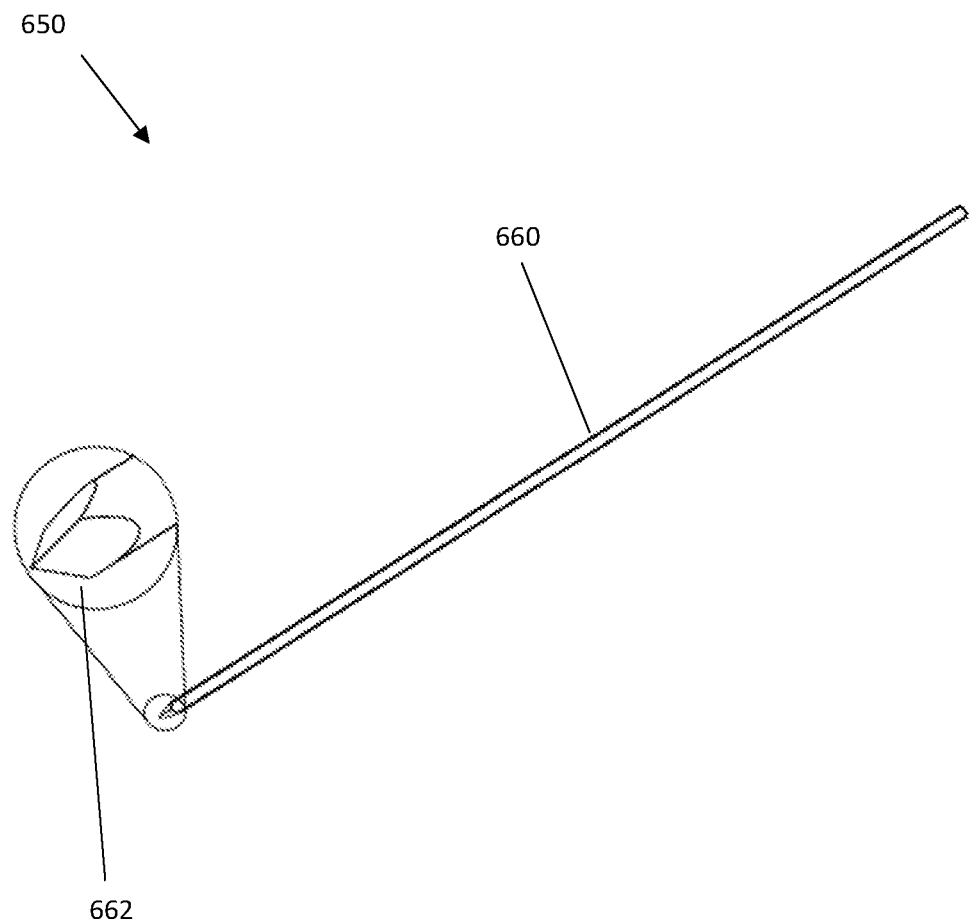
FIG. 18 is an isometric perspective view of a guide wire with an exploded view of a guide wire tip.

Further still, FIG. 18 illustrates a guide wire 650. As will further be described below, and as shown in the figures, a number of guide wires 650 may be used simultaneously during the medical procedure, although a single guide wire will be described. Of course, guide wires have different sizes and proportions could similarly be used. The guide wire 650 consists of a guide wire shaft 660 and a guide wire tip 662. The guide wire shaft 660 is smooth to slide easily in any of the cannula features described in this specification. The guide wire tip 662 can be rounded, pointed, threaded, or be in any number of designs depending on the physician's objective. In the illustrated embodiment, the tip 662 is shown in a trocar design that can cut bone. The guide wire 650 can also have both ends pointed if desired, but in this embodiment the tip 662 is pointed while the opposite end is blunt. The guide wire 650 can have markings, such as a laser etch or ink mark (not shown), that define certain distances on the guide wire 650. For example, a laser etch on the guide wire 650 could be used in conjunction with depth gauge measurements 465.

In addition to all the components described so far, a kit 1200 can be provided. For instance, the kit 1200 could a sterilizable plastic tray 1210 or any bag, box, container, or the like for holding some or all of the components. For instance, as shown the kit 1200 may include some or all of the components described above, including the implant 100, the precision cutting guide 200, one or more alignment screws 300, the screwdriver 350, the drill bit 400, the screw guide 450, the targeting guide 500, the short tissue retractor 600, the long tissue retractor 625, and one or more guide wires 650. In other embodiments, the kit may not include all of the tools, for instance, the screwdriver 350, the drill bit 400, the screw guide 450 may be excluded since these components may already be present in an operating room. In this way, the kit can be delivered to the operating room in a sterile configuration, ready for surgery. Of course, additional components or tools can also be included in the kit that are not mentioned here, including gauze and other sanitary products, as well as other products used to make incisions and close incisions.

In addition to the components described above, as well as the kit, the present invention is also directed to a method of performing a medical procedure, such as to correct and fixate a bunion in surgery. FIGS. 19-33B illustrate such a method. Although a summary of the steps is provided below, the method could include some, but not all of the steps outlined below. Furthermore, the method may include some additional steps. Further still, the steps need not necessarily occur in the order they are described.

The general steps in the method of use are as follows: marking the patient's skin with a line over the midline of the first metatarsal; marking the patient's skin with a second line that is perpendicular to the first line; aligning the precision cutting guide with the marked lines; positioning the targeting guide on the precision cutting guide and aiming the targeting guide towards the fourth metatarsophalangeal joint, or any appropriate anatomic landmark; adjusting the one or more alignment screws on the precision cutting guide until the screws touch skin; inserting at least guide wire through targeting guide and then through the precision cutting guide into the first metatarsal; removing the targeting guide; rotating the precision cutting guide vertically and using the edge of precision cutting guide to dissect skin in an arc; placing large and small retractors in a correct position; rotating the precision cutting guide back into alignment; inserting at least two additional guide wires through the precision cutting guide into bone; inserting the screw guide; inserting a guide wire though the screw guide; creating the osteotomy; removing the precision cutting guide and guide wires that were associated with the precision cutting guide; correcting the deformity; drilling a hole for the implant over the guidewire; inserting the implant; and removing the remaining guide wire and close incisions. Additional steps may include repositioning the precision cutting guide using adjustment holes if needed, and measuring the screw length using the depth gauge.

Figure 19:
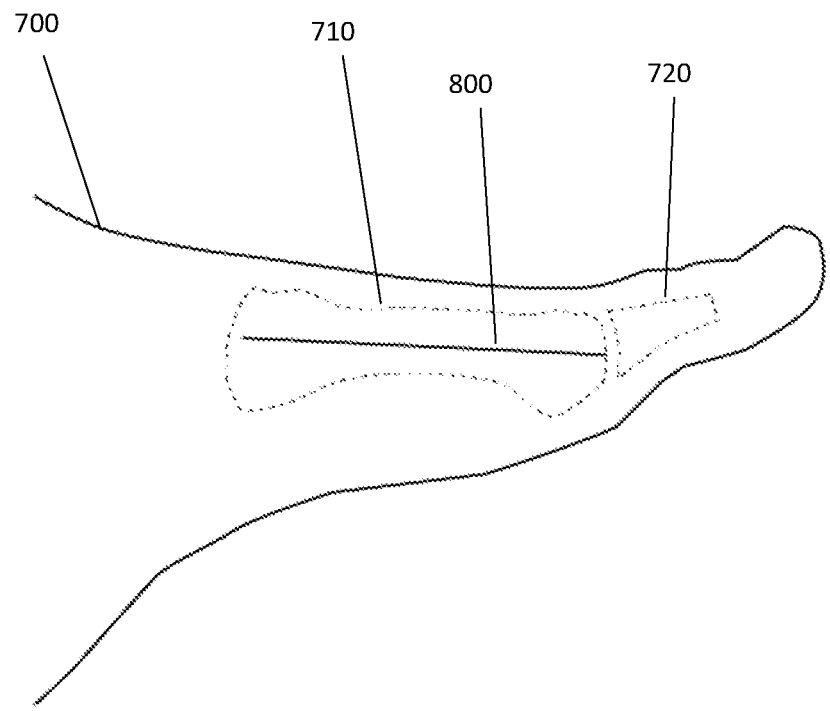
FIG. 19 is a side elevation view of a foot with a line marked on the skin.

The method of use will further be described with reference to FIGS. 19-33B. In some of these figures, the various bone features contained within the foot 700 are shown using phantom lines. Turning first to FIG. 19, a side elevation view of a patient's left foot 700 with a bunion deformity is shown. The foot 700 contains a first metatarsal 710 and a great toe proximal phalanx 720. A horizontal line 800 is drawn by a physician on the skin of the foot 700 using a radiopaque or visible surgical marker. The horizontal line 800 is situated on the skin along the centerline of first metatarsal 710.

Figure 20:
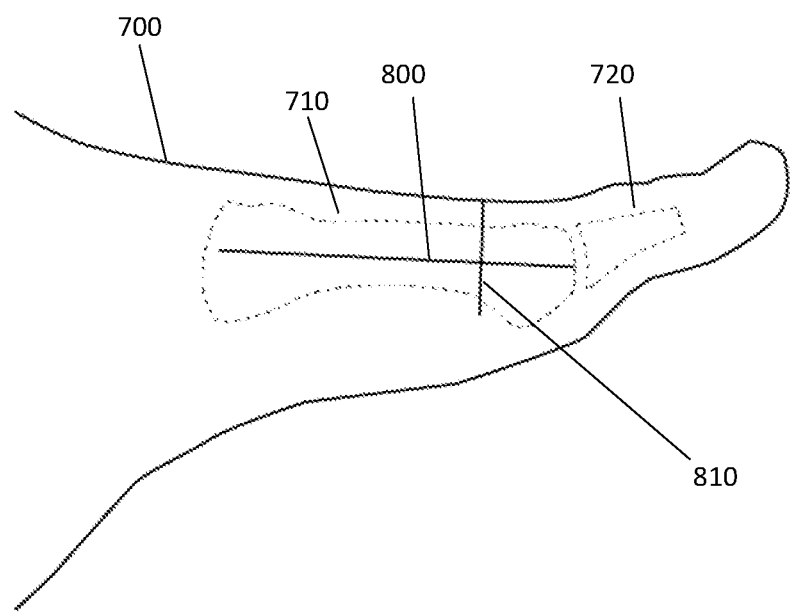
FIG. 20 is a side elevation view of the foot with two lines marked on the skin.

FIG. 20 illustrates a vertical line 810 that is marked on the skin of the foot 700 by a physician, where the vertical line 810 is perpendicular to the horizontal line 800. The vertical line 810 should cross line 800 as desired by the physician, such that an osteotomy can be created on first metatarsal 710 in the proper location.

Figure 21:
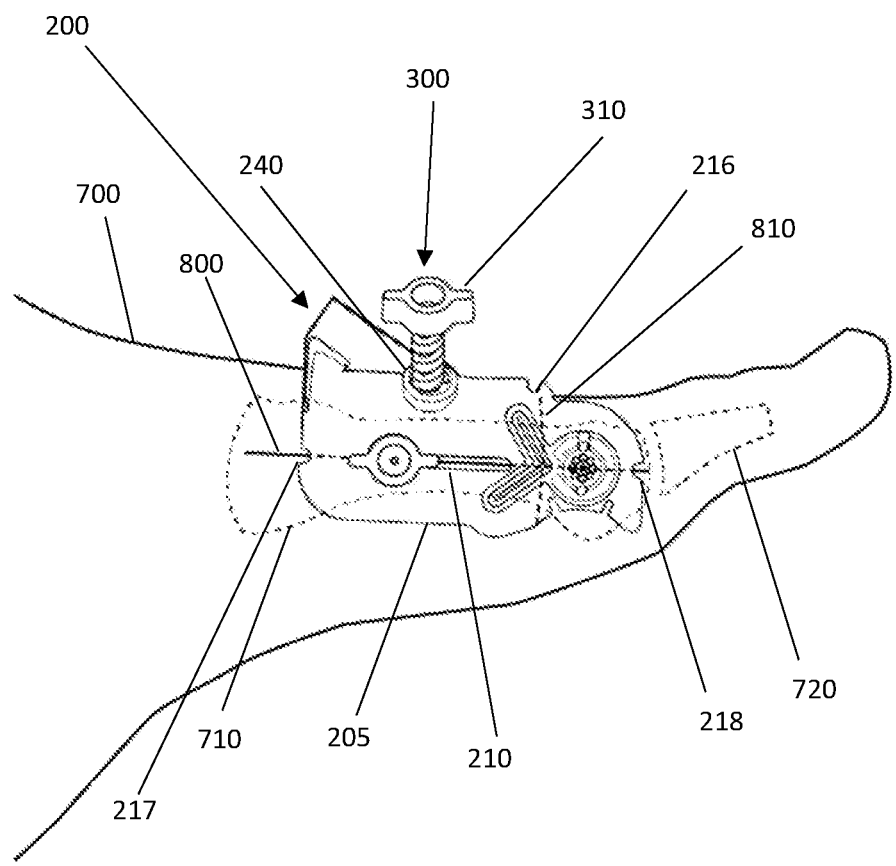
FIG. 21 is a side elevation view of the foot with the precision cutting guide positioned on the skin.

Next, FIG. 21 shows the foot 700 having the precision cutting guide 200 positioned above the skin. In this figure, the two alignment screws 300 have already been installed to the alignment holes 240, 241 of the cutting guide 200. The horizontal notches 217, 218 are positioned in line with the horizontal line 800. Additionally, the upper alignment notch 216 is positioned over the vertical line 810. The horizontal line 800 is visible through alignment slot 210.

Figure 22:
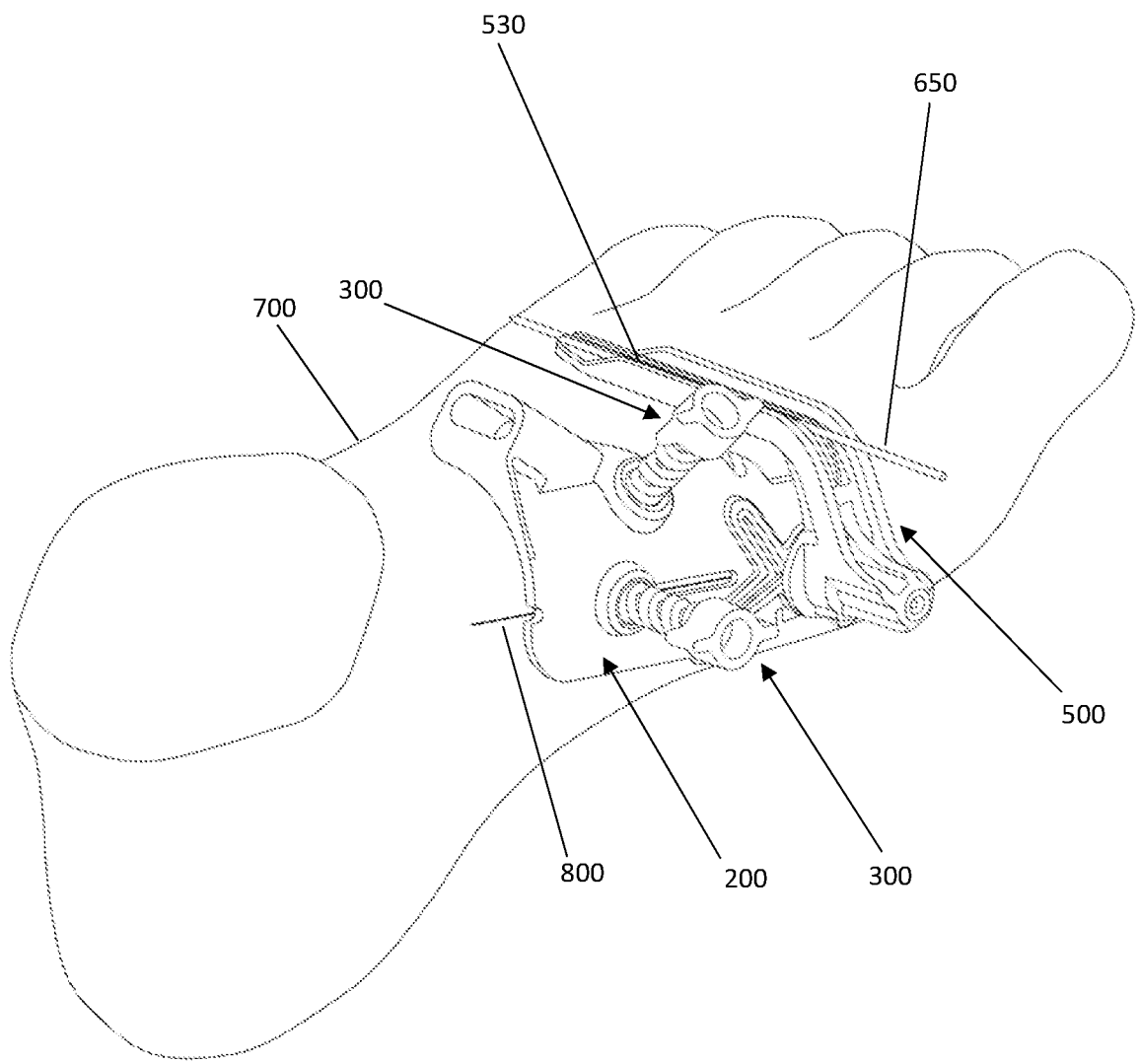
FIG. 22 is an isometric perspective view of the foot with the precision cutting guide and targeting guide in position.

FIG. 22 illustrates the foot 700 with the precision cutting guide 200 positioned properly on the foot 700 and the targeting guide 500 positioned over the precision cutting guide 200. The targeting guide recess 515 is positioned over the targeting knob 227 to form a snug and secure fit. A guide wire 650 is positioned in the groove 530 and aimed at an anatomic landmark to assist the physician in ensuring that the precision cutting guide 200 is properly positioned for the surgical procedure. In this embodiment, the targeting guide 500 and the guide 650 are positioned to aim towards the 4$^{th}$ metatarsophalangeal joint of the patient. The alignment screws 300 are adjusted by the physician to touch the skin of foot 700, which helps stabilize the precision cutting guide 200.

Figure 23:
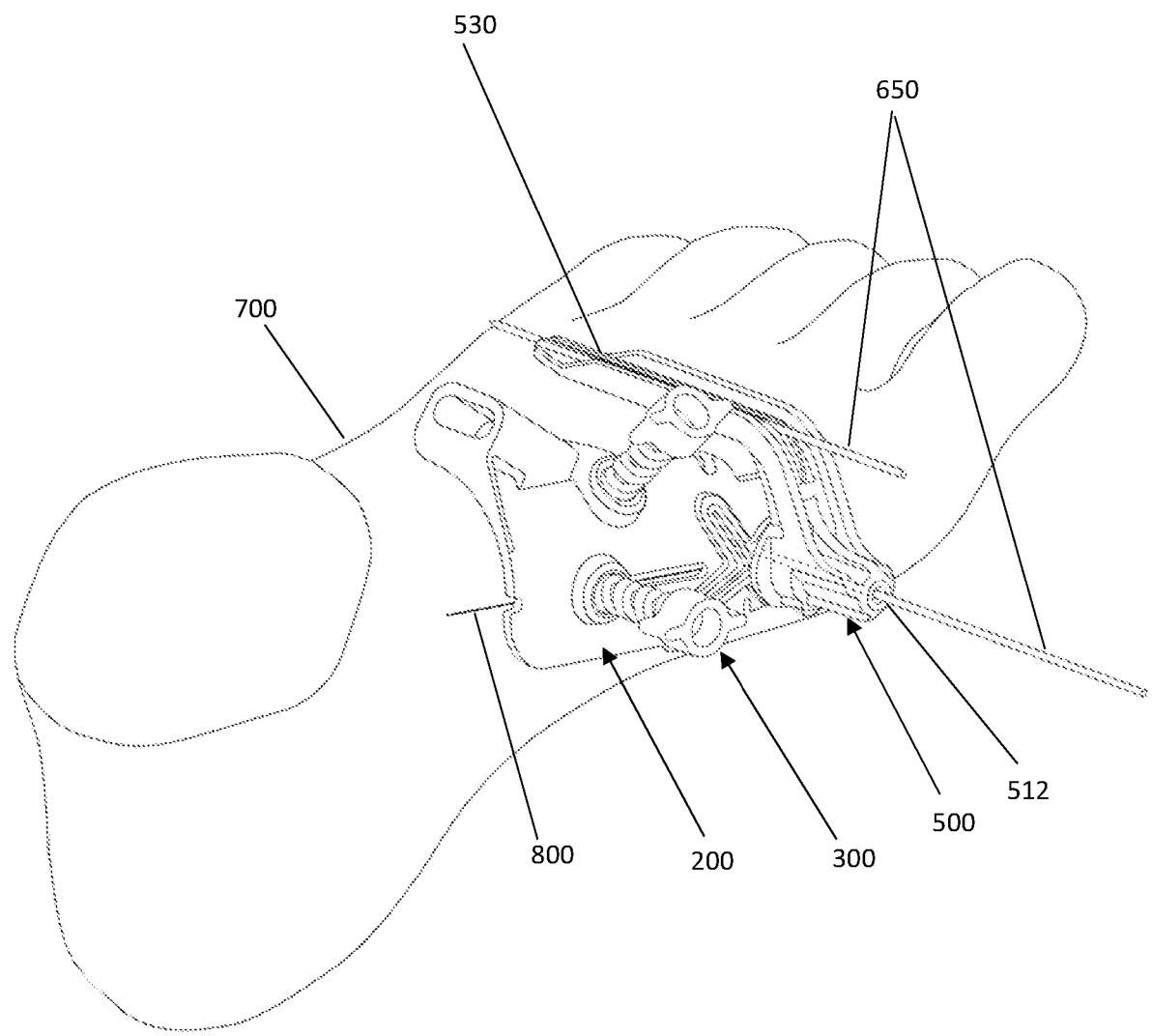
FIG. 23 is an isometric perspective view of the foot with the precision cutting guide attached to the foot with a guide wire.

Next, FIG. 23 shows the foot 700 with the precision cutting guide 200 in the proper position. In this figure, the alignment screws 300 have been tightened until they touch the skin of the foot 700, and the targeting guide 500 is positioned properly. A guide wire 650 is then inserted through the targeting guide cannula 512 and then through the center targeting hole 235, and then through the skin and into the first metatarsal 710. If desired, the physician can use fluoroscopy to confirm whether the cutting guide slot 207 is at the proper location for the surgical procedure. In this embodiment, the cutting guide insert 206 is radiopaque, causing the cutting guide slot 207 to be easily identified by the physician in fluoroscopy. If necessary, the physician can now use the adjustment holes 230 to further refine the position of the precision cutting guide 200, without the need to drill additional holes in the first metatarsal 710. Usually, the physician would want to position the cutting guide slot 207 so that it is vertically centered in the first metatarsal 710. By removing the targeting guide 500, the physician can move the precision cutting guide 200 such that the guide wire 650 passes through the desired adjustment hole 230, which has the effect of moving the cutting guide slot 207 relative to the first metatarsal 710. In this embodiment, the eight adjustment holes 230 permit vertical, horizontal, and diagonal repositioning of precision cutting guide 200.

Figure 24:
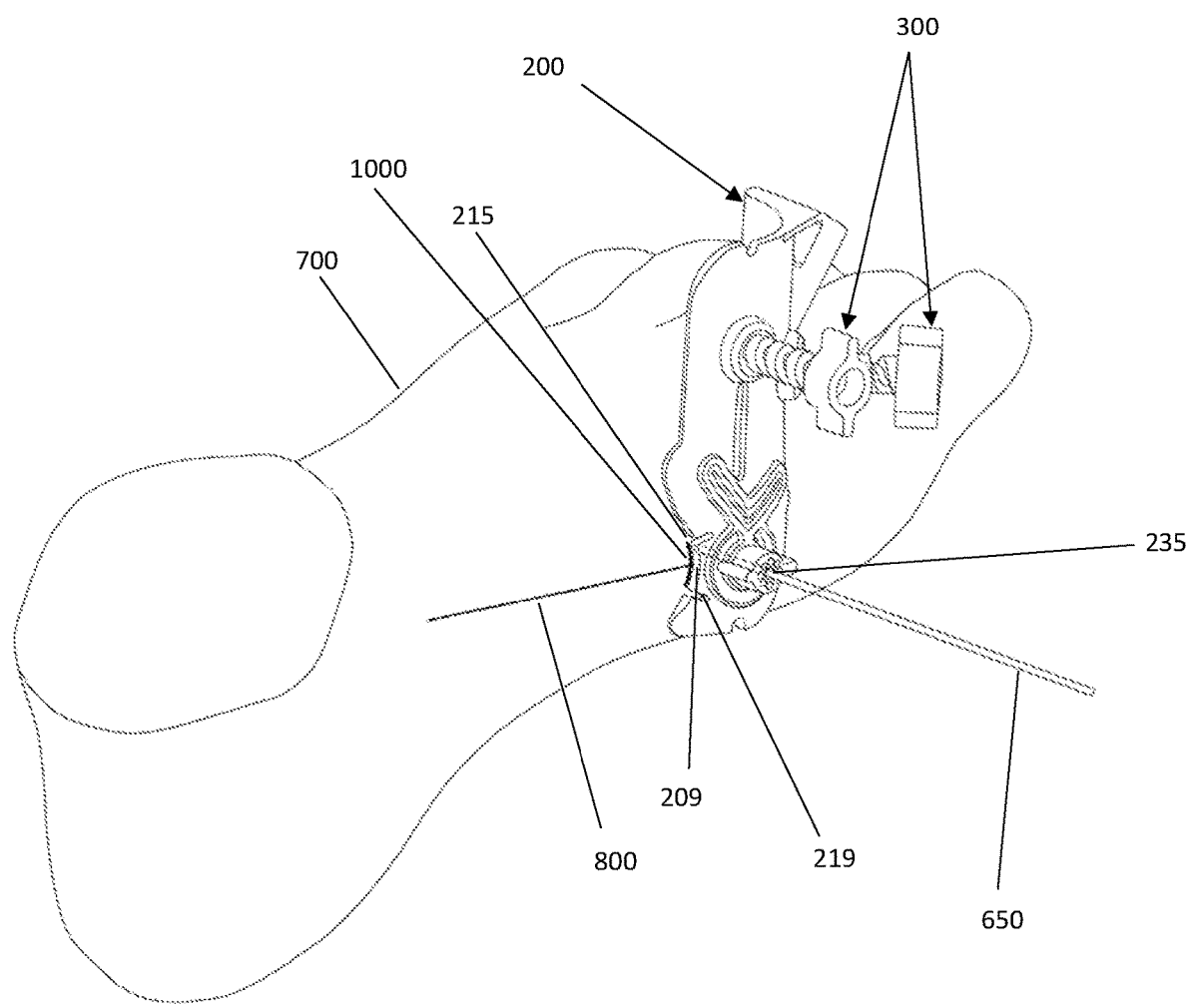
FIG. 24 is an isometric perspective view of the foot with the precision cutting guide rotated into a vertical position.

Looking next to FIG. 24, the precision cutting guide 200 is rotated approximately 90 degrees relative to the foot 700 about the guide wire 650. The targeting guide 500 has been removed and is no longer needed in this method of surgery. In this vertical position, the utility of the edge 209 is revealed. The physician can now use a scalpel or cutting tool to make a tissue incision 1000 in the foot 700 along the curvilinear path of the edge 209. Of course, where the edge 209 is a straight edge or an edge having a different curvilinear path, the incision would mirror the shape and length of the edge 209. The physician can start at either lower notch 215 or 219, and proceed to the other notch, thus creating a curved incision at the proper location with a known length. In this embodiment, the length of the incision would be 1 centimeter, because that is the curvilinear distance along the edge 209 between notches 215 and 219. Of course, the length of the incision could vary based on any number of factors.

Figure 25:
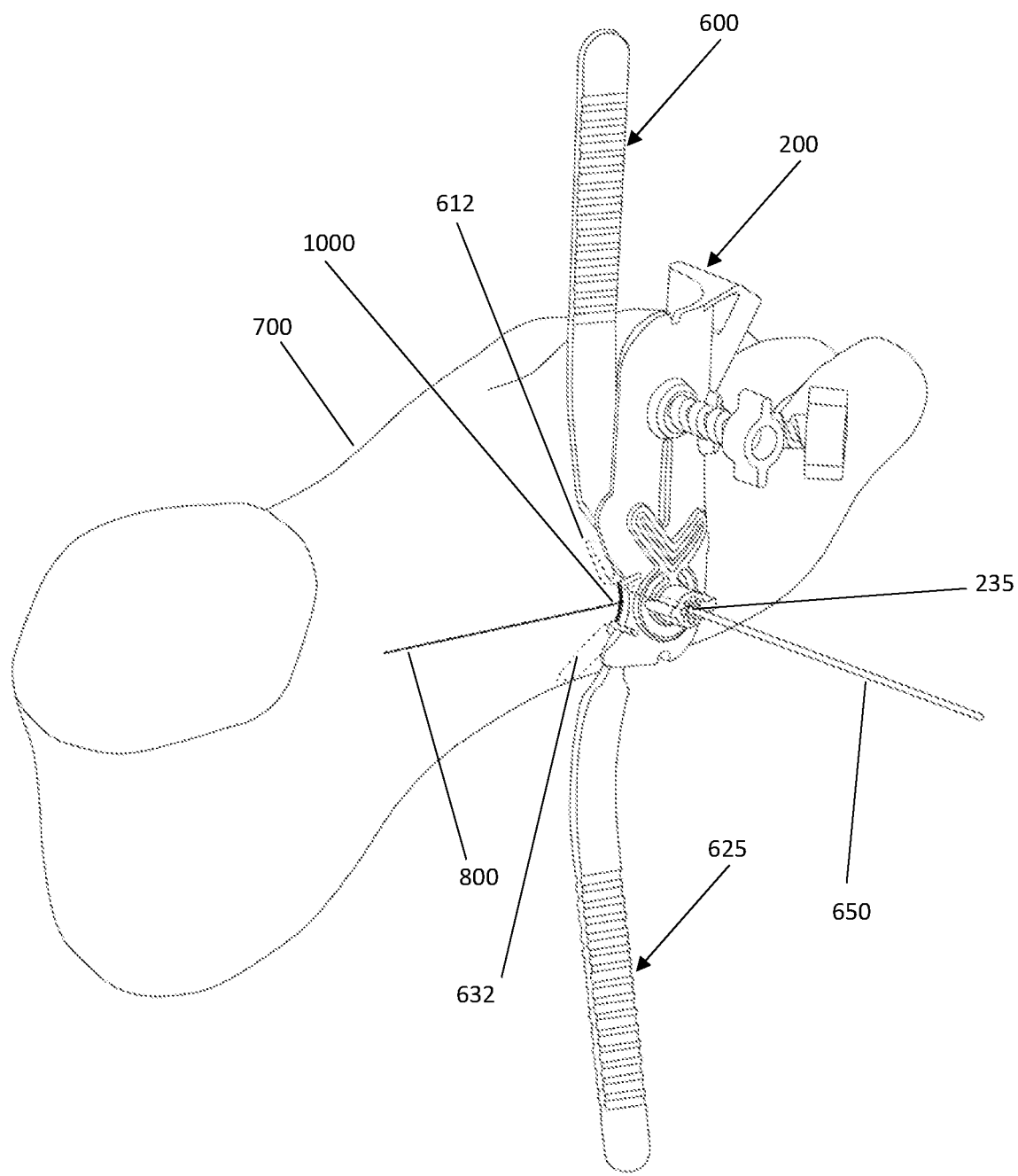
FIG. 25 is an isometric perspective view of the foot with retractors in position.

Next, the retractors 600, 625 are used. More specifically, FIG. 25 illustrates the foot 700 with the retractors 600, 625 in position to retract soft tissue away from the first metatarsal 710 underneath. Either retractor 600, 625 can be used, or both, as desired by the physician. The guide wire 650 is shown in the center targeting hole 235, however as noted previously, the physician can use any of the adjustment holes 230 to allow more precise positioning of the precision cutting guide 200.

Figure 26:
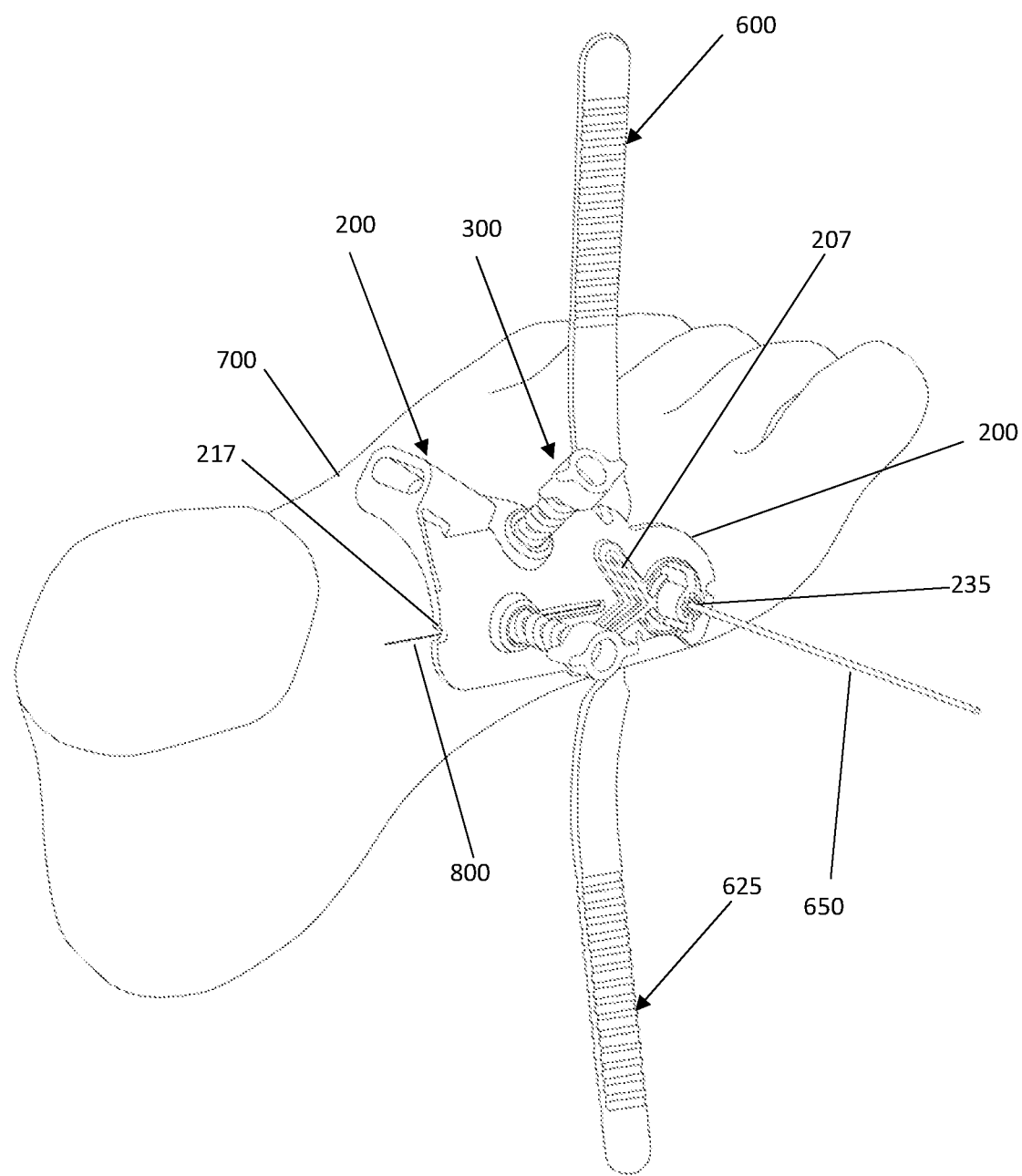
FIG. 26 is an isometric perspective view of the foot with the precision cutting guide rotated to horizontal position and the retractors in position.

FIG. 26 show the foot 700 with the retractors 600, 625 in position on soft tissue, after the precision cutting guide 200 has been rotated back to the horizontal position and over the retractors 600, 625. The precision cutting guide 200 is realigned with the horizontal line 800 such that the line 800 is visible in the alignment slot 210. Due to the design of the precision cutting guide 200, the tissue incision 1000 made by cutting tissue along the edge 209 will now fall directly under the cutting guide slot 207. The physician now has access to the first metatarsal 710 through the cutting guide slot 207.

Figure 27:
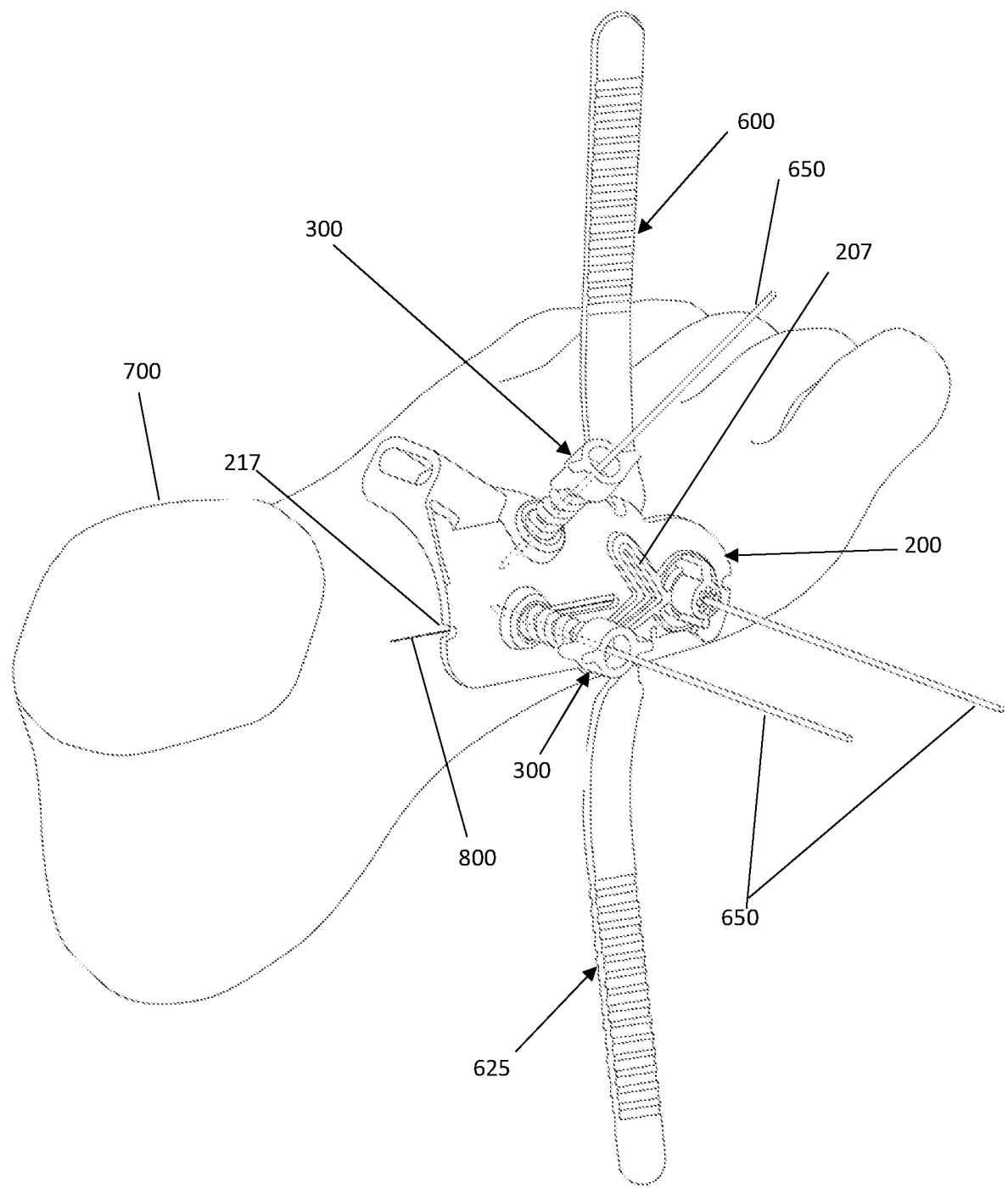
FIG. 27 is an isometric perspective view of the foot with the precision cutting guide in a horizontal position and multiple guide wires installed.

Next, FIG. 27 illustrates the precision cutting guide 200 in position on the foot 700, with the cutting guide slot 207 positioned over the skin incision 1000. The physician can anchor the precision cutting guide 200 with additional guide wires if desired. For instance, guide wires 650 are shown passing through the cannula 320 of both alignment screws 300, into the upper and lower alignment holes 240, 241 of the precision cutting guide 200, and then continuing through skin until the guide wires 650 reach the first metatarsal 710. There are three guide wires 650 shown anchoring the precision cutting guide 200 to the first metatarsal 710. In this embodiment, the three guide wires 650 anchored into the first metatarsal 710, and the two alignment screws 300 pressing against skin, plus the shape and contour of the precision cutting guide 200, all combine to create a stable and secure attachment to the foot 700 in preparation for an osteotomy.

Figure 28:
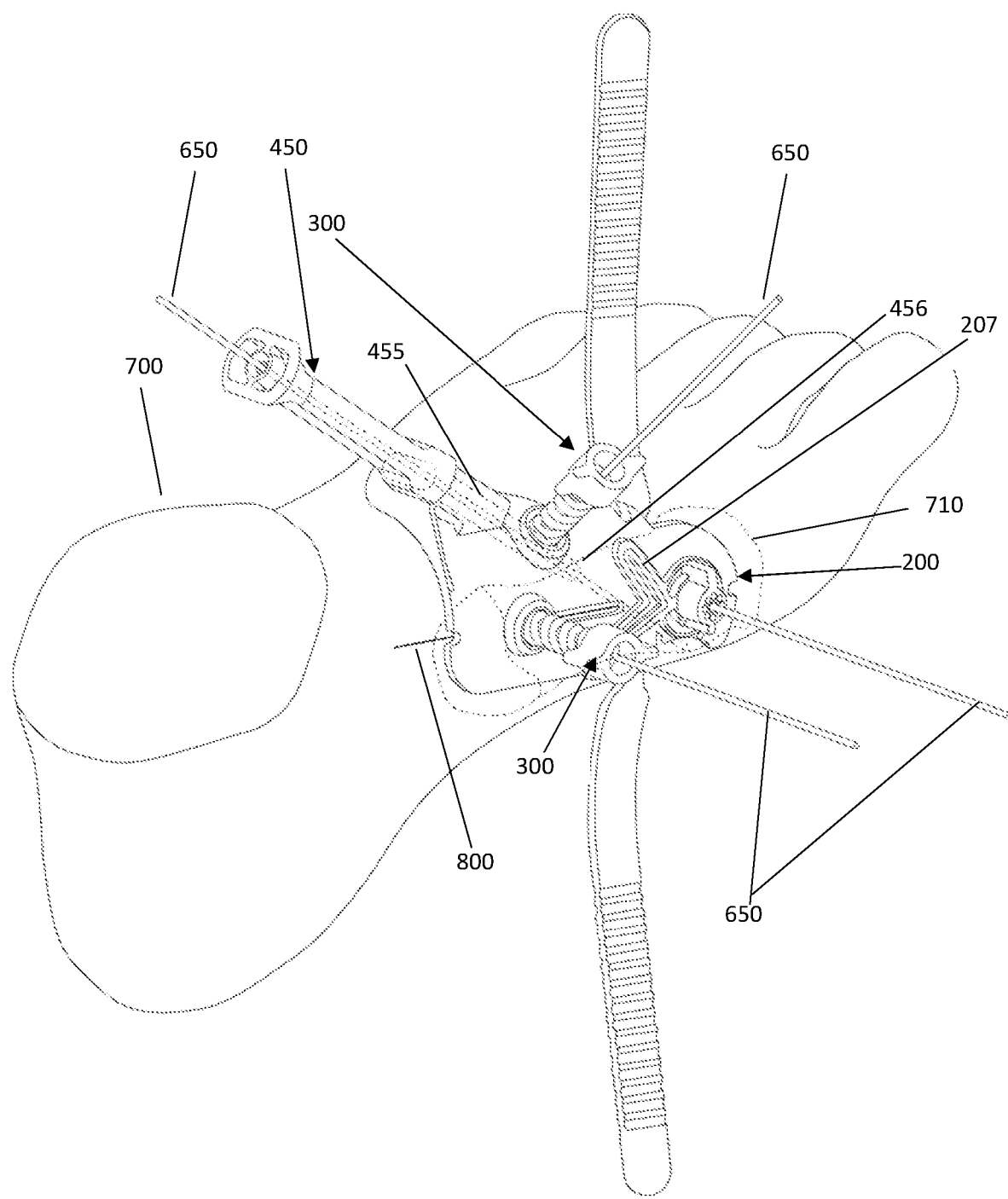
FIG. 28 is an isometric perspective view of the foot with a screw guide inserted into the precision cutting guide.

FIG. 28 illustrates the next step in the surgical procedure, in which the screw guide 450 has been inserted into the guide tube slot 250. Tissue protector sleeve 455 is designed such that it can move side to side within guide tube slot 250. An additional guide wire 650 has been inserted into the screw guide 450, and passes through the skin of the foot 700 into the first metatarsal 710. The physician can use fluoroscopy if desired to ensure the guide wire 650 is in the proper location of the first metatarsal 710, and the physician can reorient the tissue protector sleeve 455 in the guide tube slot 250, if needed. The physician can then use the depth gauge measurements 465 to determine the length of implant needed for surgery.

Figure 29A:
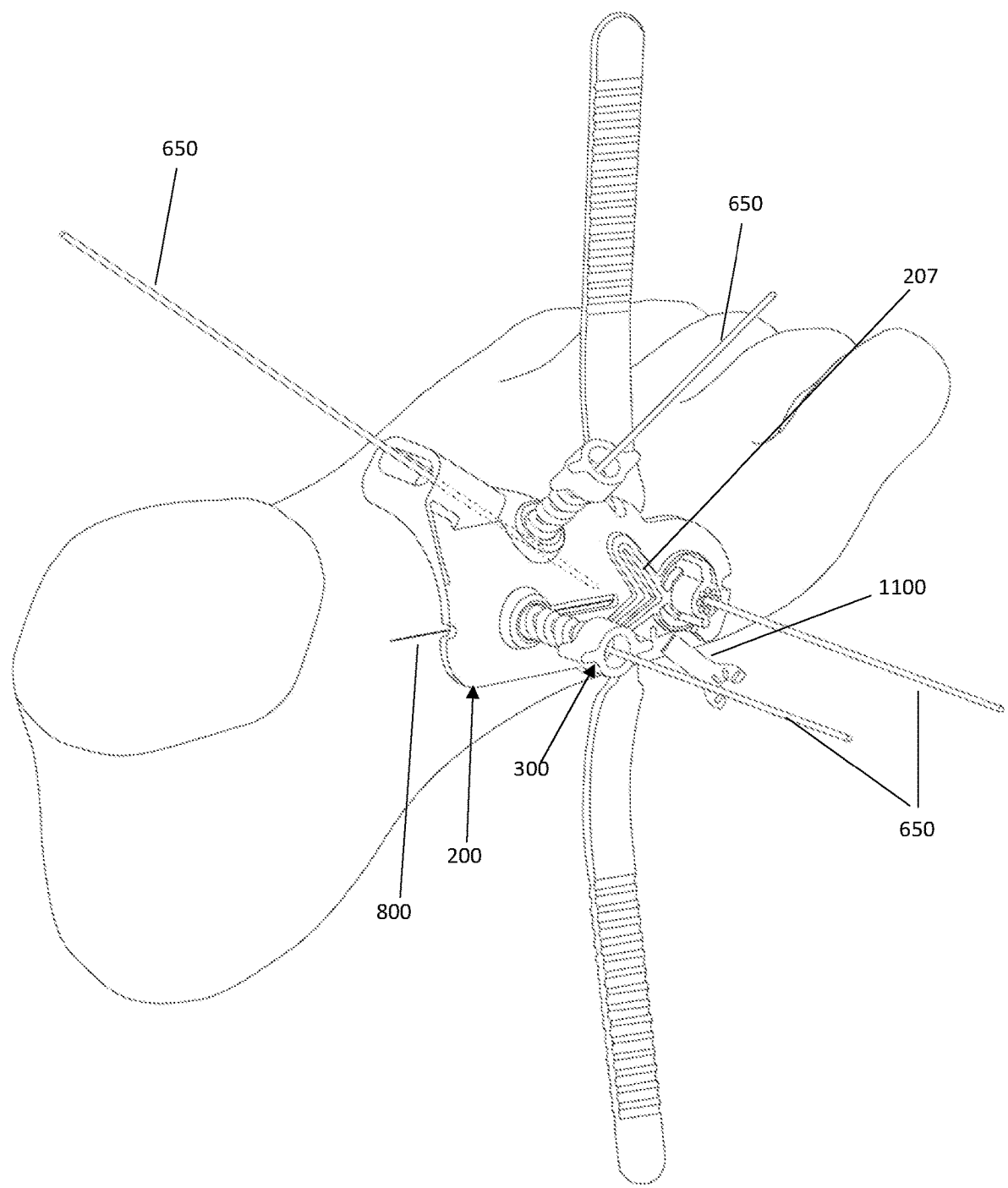
FIG. 29A is an isometric perspective view of a foot with osteotomy created in a bone.
Figure 29B:
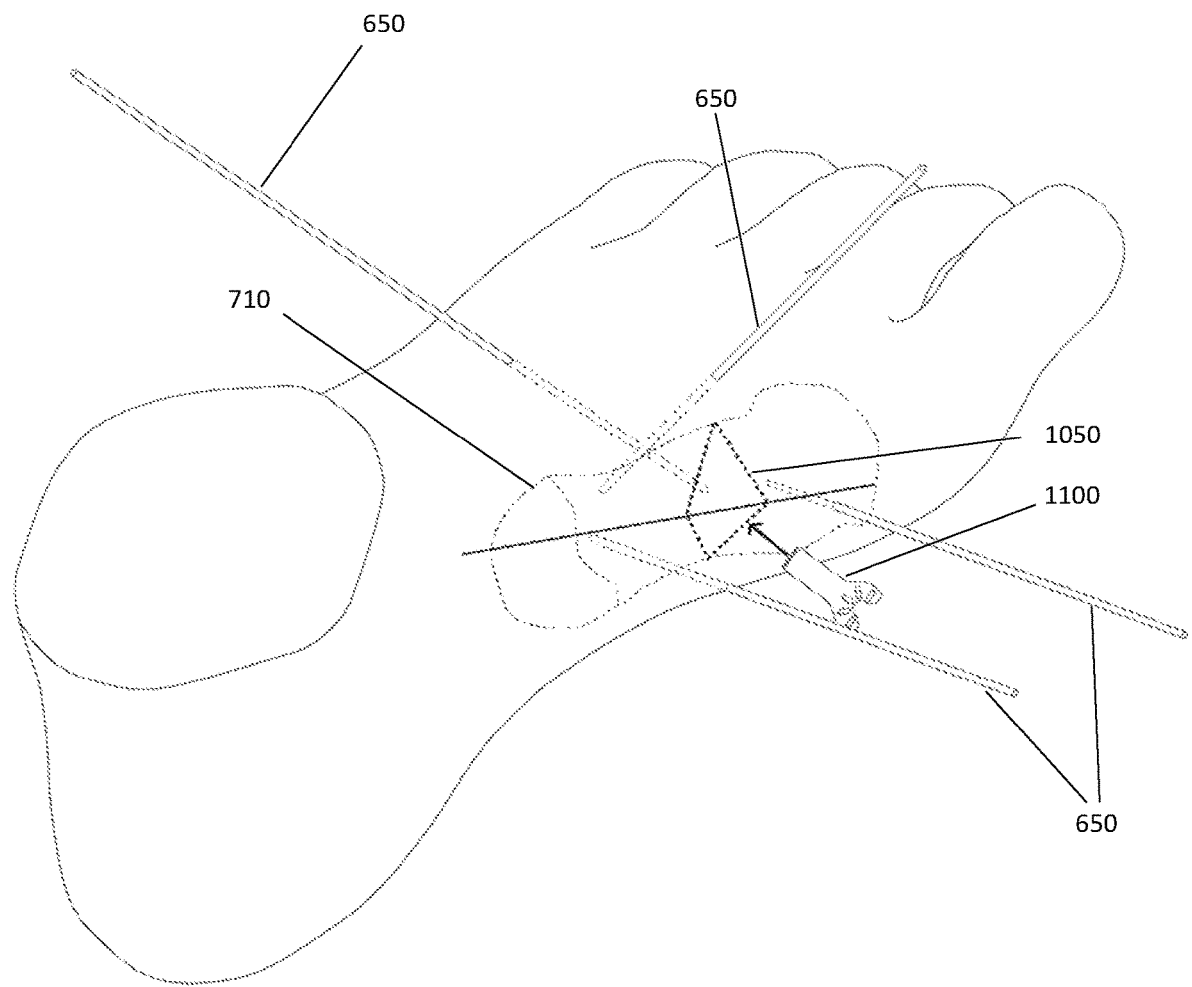
FIG. 29B is an isometric perspective cutaway view of a foot with osteotomy created in a bone with the components within the foot shown in phantom.

FIG. 29A shows the guide wire 650 associated with the guide tube slot 250 partially removed so that the guide wire 650 is no longer underneath the cutting guide slot 207. In addition, the screw guide 450 has been removed. The physician can now use a cutting instrument such as bone saw 1100, cutting bur, scalpel or other instrument to pass through the cutting guide slot 207, through the skin incision into first metatarsal 710, and create an osteotomy in the first metatarsal 710. The first metatarsal 710 now is separated such that first metatarsal fragment 711 is detached from the remainder of first metatarsal 710. FIG. 29B is a cutaway view without the components other than the guide wires 650 to better show what is occurring to the first metatarsal 710. The bone saw 1100 is intersecting the first metatarsal 710 such that it creates the osteotomy 1050. Although the osteotomy 1050 appears as a polygon in FIG. 29B, it is the extension of bone saw 1100 making a V-shaped cut through cylindrical and curved first metatarsal 710 based on the shape of the cutting guide slot 207.

Figure 30:
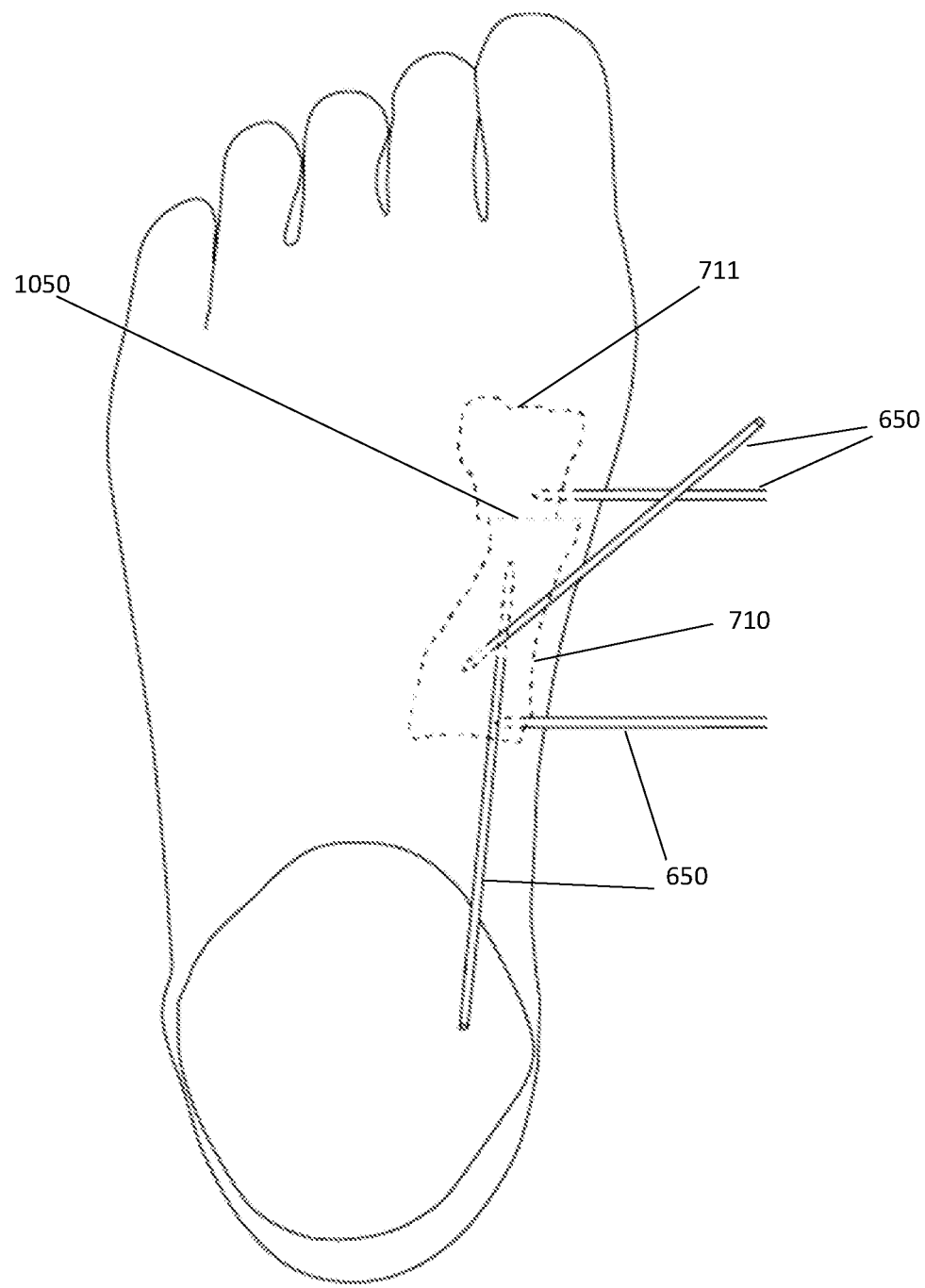
FIG. 30 is a top plan view of a foot with the deformity corrected with the components within the foot shown in phantom.

FIG. 30 is a top plan view of the foot 700 after the physician has corrected the deformity by using the osteotomy to realign first metatarsal fragment 711 in the desired position, where the various bone components are shown in phantom, without the components other than the various guide wires 650 to better show what is occurring.

Figure 31:
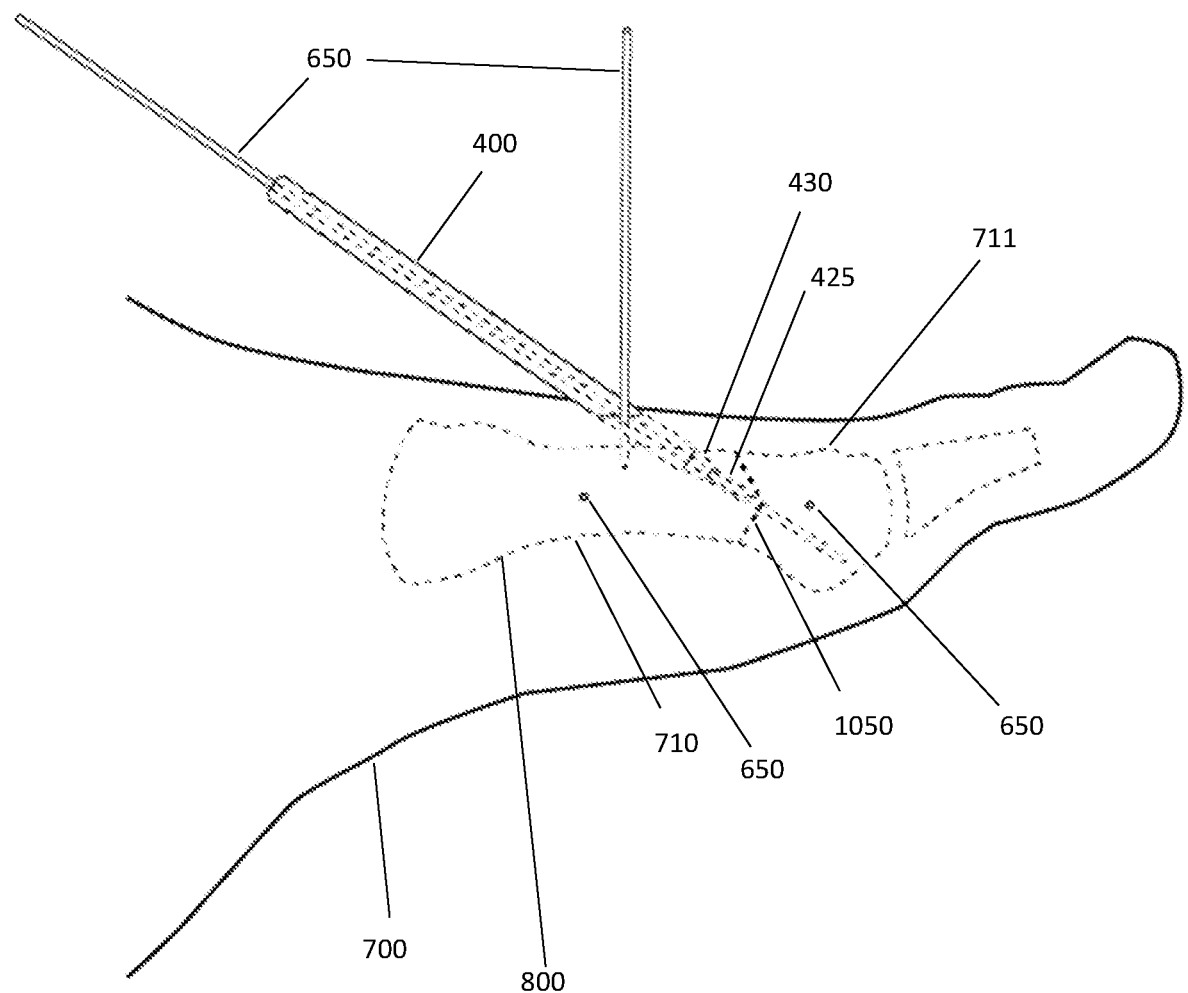
FIG. 31 is a side elevation view of a foot with the deformity corrected and hole being drilled with the components within the foot shown in phantom.

FIG. 31 shows the foot 700 with a hole being drilled for an implant. Here, the guide wire 650 has been reinserted into first metatarsal fragment 710. The drill bit 400 is placed over the guide wire 650 and a hole is drill in first metatarsal 710. The design of drill bit 400 creates a hole in first metatarsal 710 for implant 100 as well as countersink area for implant head 110.

Figure 32:
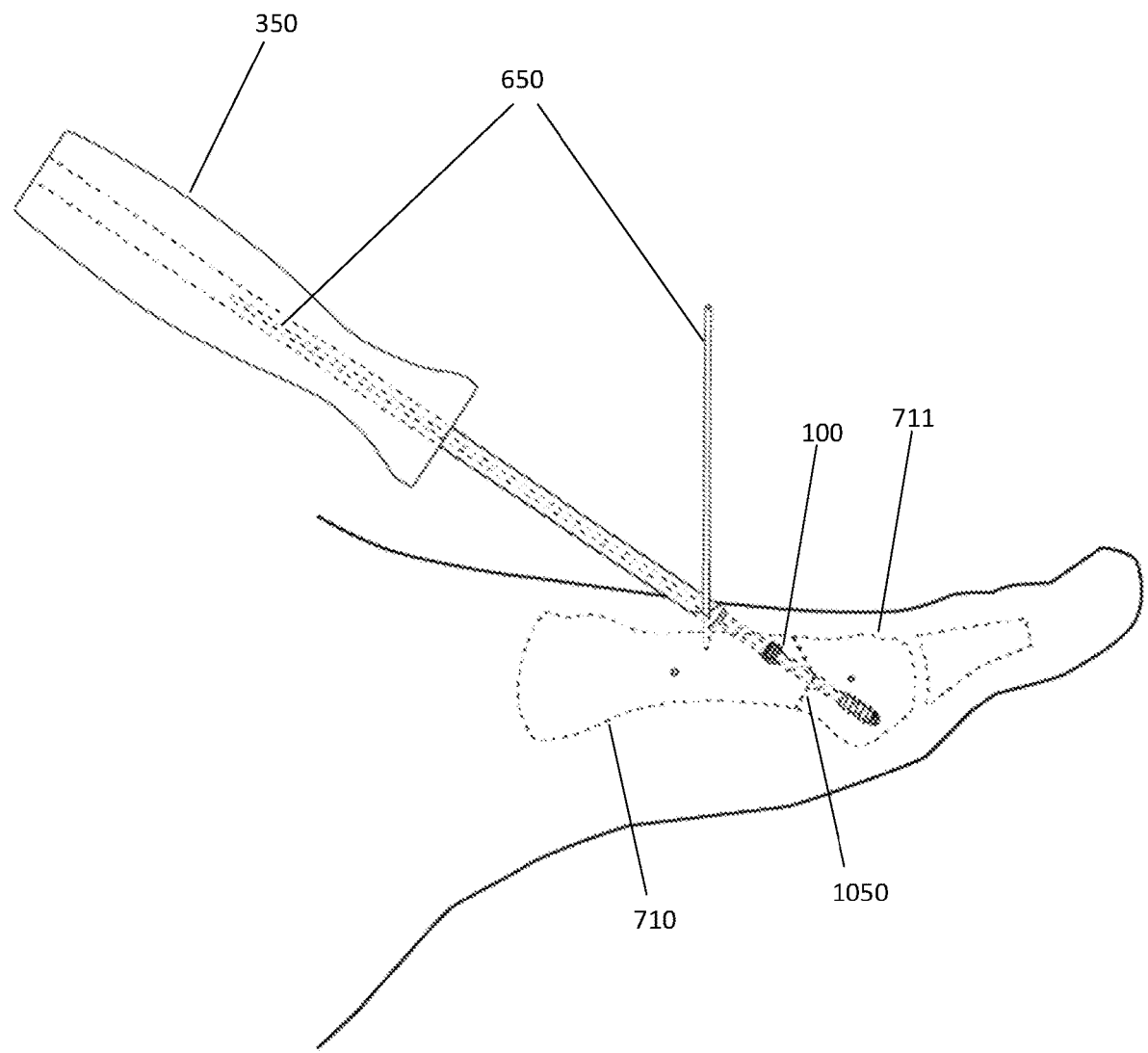
FIG. 32 is a side elevation view of a foot with implant placed to fixate bones with the components within the foot shown in phantom.

FIG. 32 illustrates the foot 700 where the implant 100 is fixates the first metatarsal 710 to first metatarsal fragment 711, after the deformity has been corrected. The cannulated screwdriver 350 is used to drive the implant 100 to the proper location in the bone. The upper threads 115 are situated in the first metatarsal 710 and the distal threads 120 are situated in the first metatarsal fragment 711, which allows the head 110 to create compression between the two bones 710 and 711.

Figure 33A:
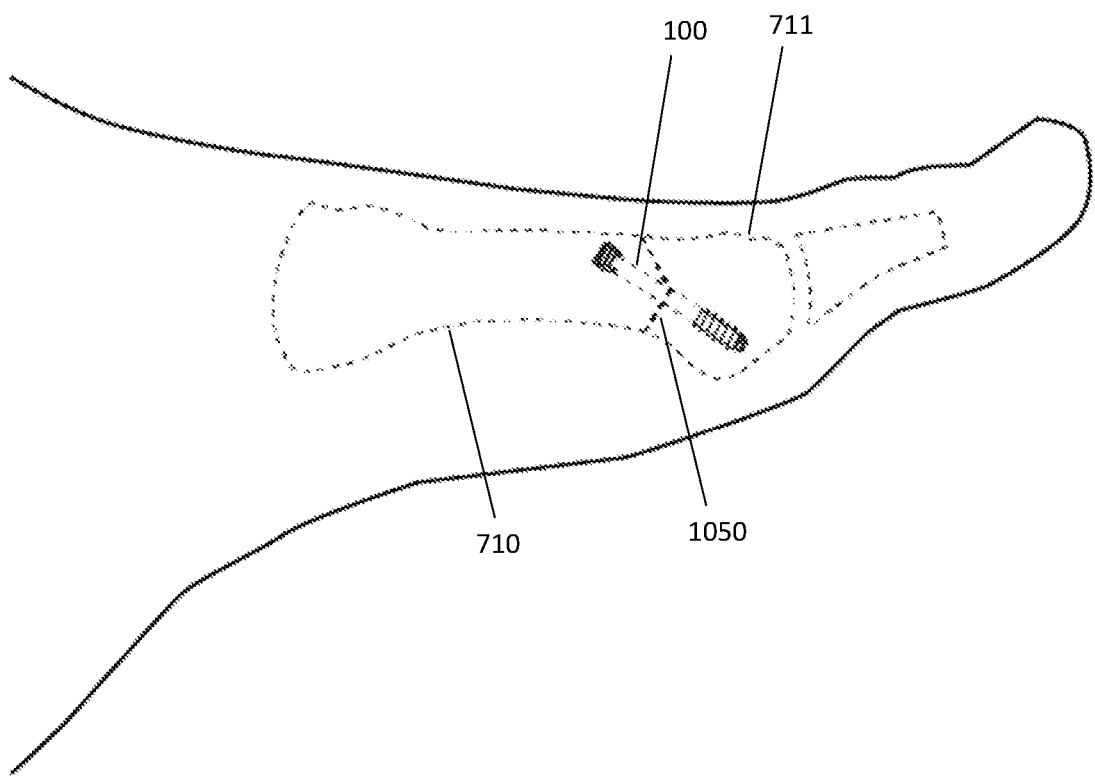
FIG. 33A is a side elevation view of a foot with deformity corrected after surgery with the components within the foot shown in phantom.
Figure 33B:
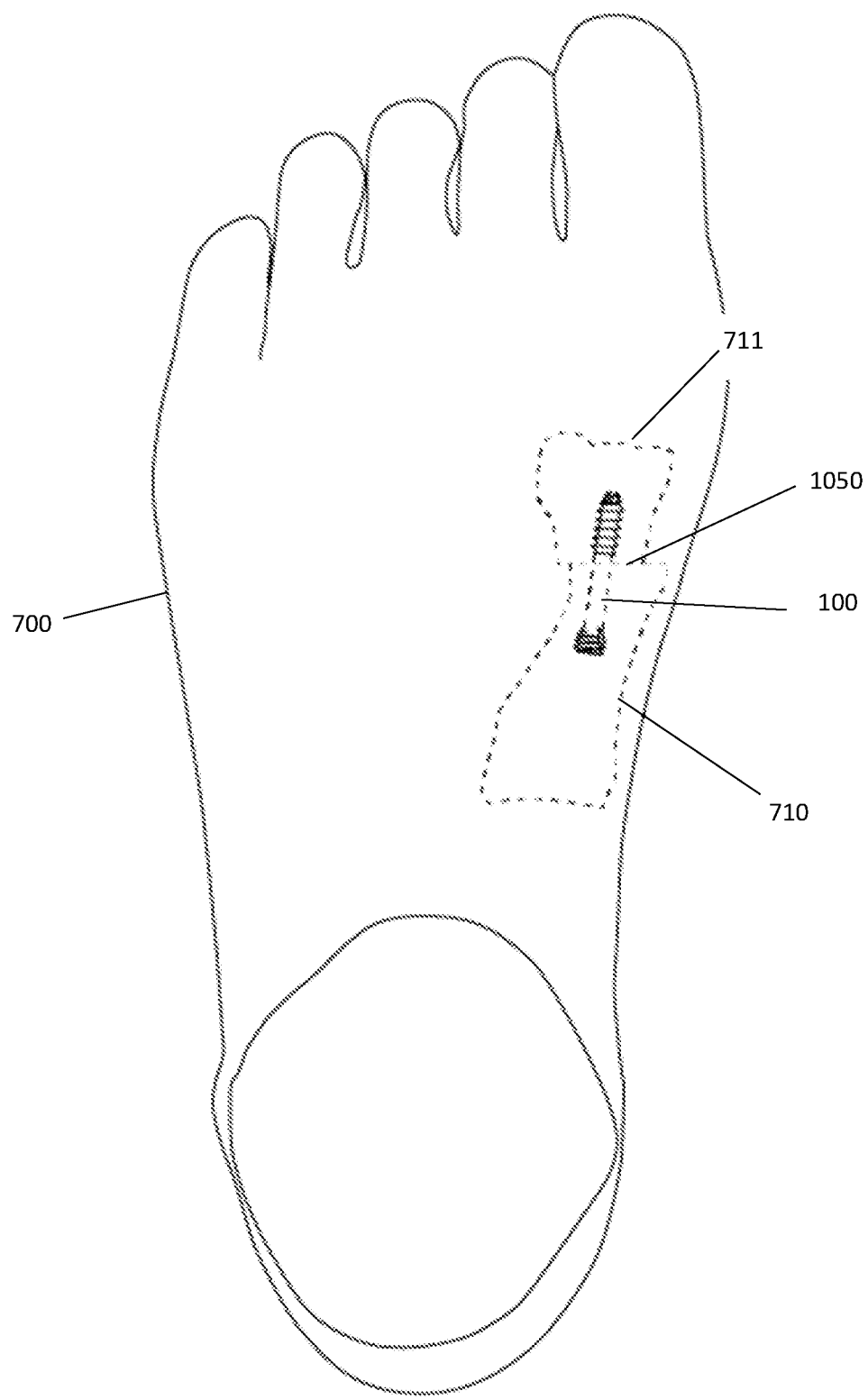
FIG. 33B is a top plan view of a foot with deformity corrected after surgery with the components within the foot shown in phantom.
Figure 34:
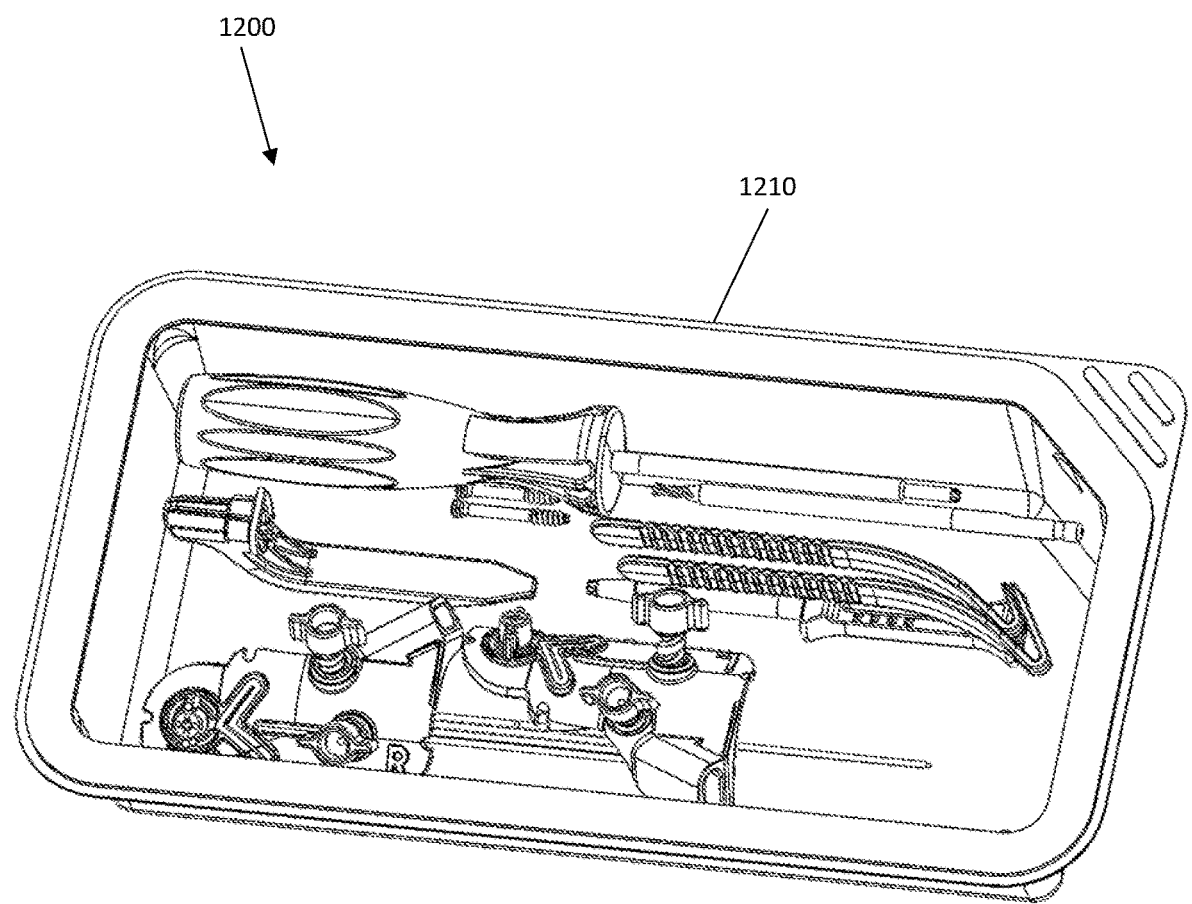
FIG. 34 is an isometric perspective view of a kit.

Finally, FIGS. 33A and 33B illustrate side elevation and top plan views of the foot 700 with all surgical instruments removed, after the incision has been closed, and the deformity has been corrected.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept. For example, any of the specific aspects of any of the described embodiments could similarly be used with any of the other embodiments. Furthermore, while specific materials have been described, it should be known that any materials could used to create any of the described drapes. For instance, materials may be chosen based on any number of criteria, including costs, availability, and various sterility properties. Moreover, as described above, the individual components need not be formed in the disclosed shapes, or assembled in the disclosed configuration, but could be provided in virtually any shape, and assembled in virtually any configuration. Further, any of the components can be manufactured with one another or be separately manufactured and later assembled. Furthermore, all the disclosed features of each disclosed embodiment can be combined with, or substituted for, the disclosed features of every other disclosed embodiment except where such features are mutually exclusive. Figures are not to scale, and some features are exaggerated to show details of particular features or method steps. Further still, some of the tools described above may be reusable, while others may be disposable.

It is intended that the appended claims cover all such additions, modifications and rearrangements. Expedient embodiments of the present invention are differentiated by the appended claims.

What is claimed is:

1. A precision cutting guide for creating an osteotomy comprising:
   a main body shaped to conform to an outside surface of a foot of a patient, the main body having:
      a first end;
      a second end opposite the first end;
      an axis extending from the first end to the second end;
      a bottom perimeter extending from the first end to the second end;
      at least one curvilinear edge extending along the bottom perimeter; and
      at least one opening;
   a cutting guide insert with a chevron-shaped cutting slot capable of receiving a cutting instrument; and
   at least one guide wire insertable into the at least one opening;
   wherein the main body is rotatable about the at least one guide wire between:
      a first position where the axis is substantially vertical and the curvilinear edge is located substantially along a vertical line associated with a first metatarsal; and
      a second position where the axis is substantially horizontal and the chevron-shaped cutting slot is substantially superimposed over the vertical line to enable cutting of a bone through the cutting guide.

2. The precision cutting guide of claim 1, wherein the cutting guide insert is radiopaque.

3. The precision cutting guide of claim 1, further comprising at least one alignment slot formed in the main body, wherein the at least one alignment slot is configured to allow the precision cutting guide to be aligned with the foot of the patient.

4. The precision cutting guide of claim 3, wherein the at least one alignment slot extends substantially horizontally along the main body when the main body is in the second position.

5. The precision cutting guide of claim 1, further comprising at least one notch formed along the perimeter of the main body, the notch configured to align the main body relative to the foot of the patient.

6. The precision cutting guide of claim 5, wherein the at least one notch further comprises:
- at least one horizontal notch formed in the main body and extending substantially horizontally when the main body is in the second position; and
- at least one upper alignment notch formed in the main body and extending substantially vertically when the main body is in the second position.

7. The precision cutting guide of claim 5, further comprising first and second lower notches formed in the main body;
  wherein the first and second lower notches extend from the curvilinear edge.

8. The precision cutting guide of claim 7, wherein the distance between first and second lower notches along the curvilinear edge is approximately one centimeter.

9. The precision cutting guide of claim 1, further comprising a targeting knob extending from the main body with at least one hole formed therein.

10. The precision cutting guide of claim 9, wherein the at least one hole formed in the targeting knob further comprises:
- a center targeting hole; and
- at least one additional adjustment hole located proximate to the center targeting hole.

11. The precision cutting guide of claim 10, wherein the at least one additional adjustment holes further comprises
- a first adjustment hole located vertically above the center targeting hole;
- a second adjustment hole located vertically below the center targeting hole;
- a third adjustment hole located horizontally to the left of the center targeting hole; and
- a fourth adjustment hole located horizontally to the right of the center targeting hole.

12. The precision cutting guide of claim 10, further comprising a targeting guide comprising:
- a body;
- a recess formed in the body configured to engage with the targeting guide attached to the main body; and
- a cannula extending through the body and configured to receive a guide wire.

13. The precision cutting guide of claim 1, further comprising a guide tube slot formed in the main body that is substantially perpendicular to the cutting slot.

14. The precision cutting guide of claim 13, further comprising:
- a screw guide releasably insertable into the guide tube slot; and
- an orthopedic implant rotatable by the screw guide and configured to fixate first and second bone sections.

15. The precision cutting guide of claim 1, wherein in the first position the main body is configured to enable a curvilinear incision to be made in tissue of the foot; and
  wherein in the second position the main body is configured to enable cutting of a bone through the cutting guide and through the curvilinear incision.

16. The precision cutting guide of claim 15, further comprising at least one retractor configured to engage with tissue of the foot when the main body is in the first position; and
  wherein the at least one retractor remains engaged when the main body is rotated to the second position.

17. A precision cutting guide for creating an osteotomy comprising:
- a main body shaped to conform to an outside surface of a foot of a patient and having:
  - a first opening that is chevron-shaped;
  - at least one additional opening; and
  - a curvilinear lower edge;
- a cutting guide insert with a chevron-shaped cutting slot capable of receiving a cutting instrument, the cutting guide inserted into the first opening of the main body; and
- at least one guide wire insertable into the at least one additional opening;
- wherein the main body is rotatable about the at least one guide wire between:
  - a first position where the axis is substantially vertical where the main body is configured to enable a curvilinear incision to be made in tissue of the foot; and
  - a second position where the axis is substantially horizontal where the main body is configured to enable cutting of a bone through the cutting guide and through the curvilinear incision made in the tissue.

18. The precision cutting guide of claim 17, further comprising:
- a guide tube slot formed in the main body that is substantially perpendicular to the cutting slot;
- a screw guide releasably insertable into the guide tube slot; and
- an orthopedic implant rotatable by the screw guide and configured to fixate first and second bone sections.

19. The precision cutting guide of claim 17, further comprising:
- a targeting knob extending from the main body with at least one hole formed therein;
- a targeting guide comprising:
  - a body;
  - a recess formed in the body configured to engage with the targeting guide attached to the main body; and
  - a cannula extending through the body and configured to receive a guide wire.

20. A precision cutting guide for creating an osteotomy comprising:
- a main body shaped to conform to an outside surface of a foot of a patient, the main body having:
  - a perimeter having a first side end, a second side end, a top side, and a bottom side;
  - at least one curvilinear edge extending along the bottom side;
  - at least one opening configured to receive a guide wire; and
  - a chevron-shaped opening formed therein capable of receiving a cutting instrument;

wherein the main body is rotatable between:
- a first position where the curvilinear edge is located substantially along a vertical line associated with a first metatarsal to enable a curvilinear incision to be made in tissue of the foot; and
- a second position where the chevron-shaped opening is substantially superimposed over the curvilinear incision to enable cutting of a bone through the chevron-shaped opening.

* * * * *